US011413226B2

(12) United States Patent
Bourgeteau et al.

(10) Patent No.: US 11,413,226 B2
(45) Date of Patent: Aug. 16, 2022

(54) PHYLLOSILICATE COMPOSITIONS AND USES THEREOF FOR SKIN CELL REGENERATION

(71) Applicant: EPHYLA SAS, Arzal (FR)

(72) Inventors: Vincent Bourgeteau, Ferel (FR); Fabrizio Fordiani, Ploeren (FR)

(73) Assignee: EPHYLA SAS, Arzal (FR)

( * ) Notice: Subject to any disclaimer, the term of this patent is extended or adjusted under 35 U.S.C. 154(b) by 1023 days.

(21) Appl. No.: 15/768,752

(22) PCT Filed: Oct. 17, 2016

(86) PCT No.: PCT/IB2016/056230
§ 371 (c)(1),
(2) Date: Apr. 16, 2018

(87) PCT Pub. No.: WO2017/064686
PCT Pub. Date: Apr. 20, 2017

(65) Prior Publication Data
US 2021/0085577 A1 Mar. 25, 2021

Related U.S. Application Data

(60) Provisional application No. 62/242,094, filed on Oct. 15, 2015.

(51) Int. Cl.
| *A61K 8/26* | (2006.01) |
| *A61K 8/06* | (2006.01) |
| *A61K 8/25* | (2006.01) |
| *A61Q 17/04* | (2006.01) |
| *A61Q 19/00* | (2006.01) |

(52) U.S. Cl.
CPC ............. *A61K 8/26* (2013.01); *A61K 8/062* (2013.01); *A61K 8/25* (2013.01); *A61Q 17/04* (2013.01); *A61Q 19/00* (2013.01); *A61K 2800/30* (2013.01); *A61K 2800/33* (2013.01); *A61K 2800/80* (2013.01)

(58) Field of Classification Search
None
See application file for complete search history.

(56) References Cited

FOREIGN PATENT DOCUMENTS

| DE | 102005003708 | | 8/2006 |
| FR | 2955771 | | 8/2011 |
| FR | 2976503 | | 12/2012 |
| FR | 2952814 | | 7/2013 |
| KR | 101144372 | * | 4/2011 |

OTHER PUBLICATIONS

KR101144372 Translation from Google Patents (Year: 2011).*
Anonymous: "Radish root—alternative to phenoxyethanol and paraben preservative—Truth in Aging", Oct. 1, 2011 (Oct. 1, 2011), XP055320147, Retrieved from the Internet: URL:https://www.truthinaging.com/review/radish-root-alternative-to-phenoxyethanol-and-paraben-preservatives [retrieved on Nov. 16, 2016].
Anonymous: "Body Lotion for Stretch Marks: M&W", Mar. 28, 2015 (Mar. 28, 2015), XP055319962, Retrieved from the Internet: URL:https://web.archive.org/web/20150328020947/http://www.mewskinprogam.com/en/latte-corpo-antismagliature.html [retrieved on Nov. 16, 2016].
Anonymous: "Function", Jul. 29, 2015 (Jul. 29, 2015), XP055319660, Retrieved from the Internet: URL:http://www.ephyla.fr/wp-content/uploads/premium/Ephyla_FT Frametime CX_240512-ENG.pdf [retrieved on Nov. 15, 2016].
Anonymous: "Frametime CHA | Ephyla", Aug. 14, 2014 (Aug. 14, 2014), XP055319680, Retrieved from the Internet: URL: https://web.archive.org/web/20140814055519/http://www.ephyla.fr/product/frametime-cha/ [retrieved on Nov. 15, 2016].
Anonymous: "Frametime CX | Ephyla", Jul. 29, 2015 (Jul. 29, 2015), XP055319655, Retrieved from the Internet: URL:https://web.archive.org/web/20150729002709/http://www.ephyla.fr/en/product/frametime-cx/ [retrieved on Nov. 15, 2016].
Anonymous: "Frametime a Natural Cold Emulsifier", Jul. 29, 2015 (Jul. 29, 2015), XP055319657, Retrieved form the Internet: UR:http://www.ephyla.fr/wp-content/uploads/2012/11/EPHYLA_FM-Frametime_121112_ENG.pdf [retrieved on Nov. 15, 2016].
Anonymous: "MSDS (1/3) Trade Name ; Frametime CX I—Identification of Substance Trade name: Frametime CX Manufacturer/Supplier: EPHYLA sas III—Hazards Identification No Hazard Known IV—First Aid Mesures", Sep. 29, 2012 (Sep. 29, 2012), XP055319649, Retrieved from the Internet: URL:http://www.ephyla.fr/wp-content/uploads/premium/EPHYLA_MSDS-FRAMETIME CX-260912-ENG.pdf [retrieved on Nov. 15, 2016] the whole document.
Anonymous: "Sunflower oil for your skin", May 11, 2013 (May 11, 2013), XP055319717, Retrieved from Internet: URL: https://web.archive.org/web/20130511030148/http://www.botanical-online.com/english/sunflower_oil_for_your_skin.htm [retrieved on Nov. 15, 2016]

(Continued)

*Primary Examiner* — Melissa L Fisher
(74) *Attorney, Agent, or Firm* — Brouillette Legal Inc.; Robert Brouillette

(57) ABSTRACT

A Pickering formulation for use as a pharmaceutical or cosmetic composition for regenerating skin cells, allowing reducing skin stretch marks on a human skin, or healing skin cells after a burn, such as a sunburn. The Pickering formulation comprises an emulsion of oil and water phases stabilized with an organic-modified natural physosillicate, such as hectorite, montmori-Uonite, or bentonite. The pharmaceutical or cosmetic composition can be free of primary emulsifier or primary surfactant reducing as such the toxicity of the composition for the skin. As such, the pharmaceutical or cosmetic composition may consist essentially of the Pickering formulation. Indeed, it is demonstrated that the Pickering formulation can act itself as an active ingredient of the pharmaceutical or cosmetic composition leading to significant skin cell regeneration. The invention is particularly useful for reduction of stretchmarks. The Pickering formulation also boosts the sun protection factor, or SFP, of sunscreen compositions.

24 Claims, 9 Drawing Sheets

(56) References Cited

OTHER PUBLICATIONS

K. Korgavkar et al.: "Stretch marks during pregnancy: a review of topical prevention", British Journal of dermatology, vol. 172, No. 3, Feb. 8, 2015 (Feb. 8, 2015), pp. 606-615, XP055201828, ISSN: 0007-0963, DOI: 10.1111/bjd.13426.
Anonymous: "Revertime| Ephyla", Aug. 14, 2014 (Aug. 14, 2014), XP055319940, Retrieved form the Internet: https://web.archive.org/web/20140814055944/http://www.ephyla.fr/product/revertim [retrieved on Nov. 16, 2016].
Anon: "Reverteam Function: anti-aging active ingredient, anti-wrinkle collagen synthesis stimulation", Aug. 14, 2014 (Aug. 14, 2014), XP055319946, Retrieved from the Internet: URL:http://www.ephyla.fr/wp-content/uploads/premium/Ephyla_FR Revertime_300713.pdf [retrieved on Nov. 16, 2016] the whole document.
International Search Report, completion dated Nov. 17, 2016, issued in the corresponding patent application PCT/IB2016/056230 filed Oct. 17, 2016 in the name of Ephyla SAS.
XP55604348A—Aminat-G; "Preservative and Active Antimicrobial for Cosmetics", INCI Name: Glycerin and Ethyl Lauroyl Arginate HCI, Oct. 18, 2010.
XP55634001A—"AMS Leucidal Advanced-Aloe", Active Micro Systems, LLC, USA, Version 1, Sep. 16, 2010.

\* cited by examiner

PHYLLOSILICATE COMPOSITIONS AND USES THEREOF FOR SKIN CELL REGENERATION

CROSS-REFERENCE TO RELATED APPLICATIONS

The present patent application claims the benefits of priority of commonly assigned U.S. provisional Patent Application No. 62/242,094, entitled "Phyllosilicates compositions and uses thereof for skin cell regeneration" and filed at the United States Patent and Trademarks Office on Oct. 15, 2015, the content of which is incorporated herein by reference.

FIELD OF THE INVENTION

The present invention generally relates to pharmaceutical and cosmetic compositions. The compositions are Pickering formulations comprising phyllosilicate that can be used preferably for skin treatment involving skin cell regeneration such as but not limited to skin stretchmark reduction or sun burn protection and/or healing.

BACKGROUND OF THE INVENTION

Formulations and excipient used for pharmaceutical and/or cosmetic applications contain many ingredients that may be not all particularly good or safe for the skin or body. For instance, we can name surfactants used for stabilising emulsion, emulsifiers, preservatives, polyethylene glycols (or PEGs), Quats, etc. Silicone or petrochemical ingredients are also currently the only option to achieve a velvety feel of the skin, such as dimethicones, cyclemethicones, propylene glycol or the like.

Excipients known in the art may also diminish performance of active ingredients due to hot processing, interaction of petrochemicals or chemical incompatibility. Most products have a high carbon foot print and are non-sustainable and non-socially responsible because of hot water processing and non sustainable ingredients (for instance: Prop 65; Regulatory non compliant, Lack of global compliance).

Natural formulations particularly adapted for preserving the skin were developed by the inventor of the present invention.

French patent no. FR 2,952,814 B1 discloses cold emulsified composition comprising fatty phase, aqueous phase and particulate phase comprising organically modified phyllosilicates able to be positioned itself at the oil water interface to exclusively generate oil in water emulsion.

French patent no. FR 2,955,771 B1 discloses a process for preparing an active composition comprising selecting a dreg of alcoholic beverage, preferably wine, destroying at least partially the living fungi of dregs and using a part of the dregs as the active ingredient of the composition.

French patent application no. FR 2,976,503 A1 discloses the use of fatty substances useful as phyllosilicates intercalating agent to form an emulsifying particulate phase, and for generating cold opaque oil-in water emulsions.

The contents of FR 2,952,814 B1, FR 2,955,771 B1 and FR 2,976,503 A1 cited above are enclosed herein by reference.

Surfactant free formulations were first developed for being used as an excipient in the making of natural compositions with active ingredients. However, during several clinical tests using the excipient as a placebo or with an active ingredient, it has been discovered that the placebo itself has pharmaceutical or cosmetic properties and new advantages without the need of additional active ingredients. These new properties are detailed herein after.

SUMMARY OF THE INVENTION

The shortcomings of the prior art are generally mitigated by a Pickering formulation for use as a pharmaceutical or cosmetic composition for regenerating skin cells.

The invention is thus first directed to a Pickering formulation for use as a pharmaceutical or cosmetic composition for regenerating skin cells. Preferably, the regeneration of the skin cells allows reducing skin stretch marks on a human skin, or allows healing skin cells after a burn, such as but not limited to a sun burn.

According to one preferred embodiment, the pharmaceutical or cosmetic composition is free of primary emulsifier or primary surfactant.

According to one preferred embodiment, the pharmaceutical or cosmetic composition consists essentially of said Pickering formulation. It is to be understood that the Pickering formulation acts itself as an active ingredient of the pharmaceutical or cosmetic composition. It is also to be understood that other ingredients known in the art of formulation, such as non-active ingredients, secondary surfactants, can be introduced in the pharmaceutical or cosmetic composition to provide specific properties.

According to one preferred embodiment, the Pickering formulation may comprise an emulsion of an oil phase and a water phase, the emulsion being stabilized with an organic-modified natural phyllosilicate. Preferably, the emulsion may be obtained by performing the following steps:

adding an amount of said organic-modified natural phyllosilicate to said oil phase;

mixing the phyllosilicate and the oil phase to obtain a first mixture; and adding the first mixture to a water phase under stirring;

wherein said steps i, ii and ii are performed at a temperature where the oil phase is liquid, such as between 8 and 80° C., preferably between 15 and 45° C., more preferably at room temperature, for a period of time of less than 30 minutes.

According to one preferred embodiment, the organic-modified natural phyllosilicate comprises a phyllosilicate selected from the group consisting of vermiculites and smectites. More preferably, the phyllosilicate can be selected from the group consisting of sodium, potassium or calcium montmorillonites, bentonites, nonytronites, beidellites, volkonskoïtes, hectorites, saponites, sauconites, sobockites, stevensites, svinfordites and mixtures thereof. Much more preferably, the phyllosilicate is hectorite, montmorillonite, bentonite or mixtures thereof.

According to one preferred embodiment, the organic-modified natural phyllosilicate comprises an organic compound selected from the group consisting of Xanthan gum, chitosan, citric acid, glycosaminoglycans or any organic compound known in the art of Pickering formulation, such as those disclosed in French patent no. FR 2,976,503; the content of which is enclosed herewith by reference.

The invention ids also directed to a composition, preferably a surfactant free composition, for reducing the appearance of stretchmarks on a human skin, the composition comprising the Pickering formulation as defined herein.

The invention ids also directed to a sunscreen composition. The composition comprises the Pickering formulation as defined herein. The Pickering formulation provides to the sunscreen composition a synergetic effect by boosting the sun protection factor, or SEP, of said sunscreen composition. Preferably, the composition is free of primary surfactant and/or primary emulsifier.

By primary surfactant and/or primary emulsifier it is understood ionic surfactant such as Sodium Dodecyl Sulfate (SDS); Sodium Lauryl Sulfate; Sodium Olefin Sulfonate; mono or diglycerides of fatty acids; polyethylene glycol (PEG) esters of fatty acids of oils; propylene glycol esters of oils or fatty acids; glycereth or polyglycereth esters of oil or fatty acids.

The invention is also directed to a method for treating and regenerating skin cells of a human skin. The method comprises the step of:
  a. providing a Pickering formulation as defined herein;
  b. applying the Pickering formulation to at least a portion of the skin in need of such treatment; and
  c. removing the Pickering formulation from the skin after a given period of time.

According to one preferred embodiment, the Pickering formulation once applied on the skin forms a film or thin layer.

According to one preferred embodiment, the treatment allows reducing stretch marks of the human skin.

According to one preferred embodiment, the treatment allows healing skin cells damaged by a burn, such as but not limited to a sun burn.

According to one preferred embodiment, it is disclosed the use of an intercalated clay for the making of a Pickering emulsion used for pharmaceutical and/or cosmetic applications.

According to one preferred embodiment, it is disclosed the use of a pickering formulation for reducing the appearance of stretch marks on the skin.

According to one preferred embodiment, it is disclosed the use of a Pickering formulation for boosting the sun protection factor (SFP) of a sunscreen composition.

According to one preferred embodiment, it is disclosed the use of a Pickering formulation for the making of a film-forming composition to be applied on the skin.

According to one preferred embodiment, it is disclosed a process for the making of a Pickering formulation in accordance with the present invention.

Some of the advantages of the formulations in accordance with the present invention are:
  a. Making formulations that mimic the skin's natural processes;
  b. Lowering risk of irritations due to the use of a formulation that is free of primary surfactant/emulsifier;
  c. Easy making of hypoallergenic formulations;
  d. Easy making of mineral based formulations, the minerals increasing absorption of actives by the skin;
  e. Easy making of plant based formulations;
  f. Increasing other active ingredients' efficacy and performance;
  g. Reducing ingredient decks;
  h. Reducing the energy consumption for the making of cosmetic/pharmaceutical compositions, for instance by making the compositions at room temperature.
  i. Providing physical interactions between the clay platelets of the Pickering that have collapsed to form the film on the human skin, creating as such a reservoir effect, or slow delivery system. The organic molecules of the Pickering formulation must then take a longer path to reach the skin.

Other and further objects and advantages of the present invention will be obvious upon an understanding of the illustrative embodiments about to be described or will be indicated in the appended claims, and various advantages not referred to herein will occur to one skilled in the art upon employment of the invention in practice.

BRIEF DESCRIPTION OF THE DRAWINGS

The above and other objects, features and advantages of the invention will become more readily apparent from the following description, reference being made to the accompanying drawings in which.

DETAILED DESCRIPTION OF THE PREFERRED EMBODIMENT

A novel phyllosilicate compositions and uses thereof for skin cell regeneration will be described hereinafter. Although the invention is described in terms of specific illustrative embodiments, it is to be understood that the embodiments described herein are by way of example only and that the scope of the invention is not intended to be limited thereby.

As used herein % or wt. % means weight % unless otherwise indicated. When used herein % refers to weight % as compared to the total weight percent of the phase or composition that is being discussed.

By "about", it is meant that the value of weight, %, time, or temperature can vary within a certain range depending on the margin of error of the method or device used to evaluate such weight %, time, or temperature. A margin of error of 10% is generally accepted.

By "room temperature", it is meant the temperature where the compositions have been stored and prepared. Of course, the value of room temperature may vary in accordance with the geographic localization where the formulations are made. A room temperature of between about 10 and 30° C., preferably from about 15 and 25° C., is generally accepted.

The making of organic-modified natural clays is disclosed in patent FR 2 952 814 (Bourgeteau et al.), the content of which is incorporated herewith by reference. The combination of an inorganic material (e.g. clay) with biomolecules provides an organic-inorganic hybrid material with synergetic properties. The inorganic material provides high specific area, high adsorption capacity, inert and non-toxic support and rheological modification, whereas the biomolecules provide specific biological activity, hydratation and anti-aging activity.

The clay useful for the present invention are preferably selected from the group consisting of vermiculites and smectites, and more particularly of sodium, potassium and/or calcium montmorillonites, bentonite, nonytronites, beidellites, volkonskoïtes, hectorites, saponites, sauconites, sobockites, stevensites, svinfordites and mixtures thereof. Montmorillonite and bentonite are particularly useful for the present invention.

Figure 1A:
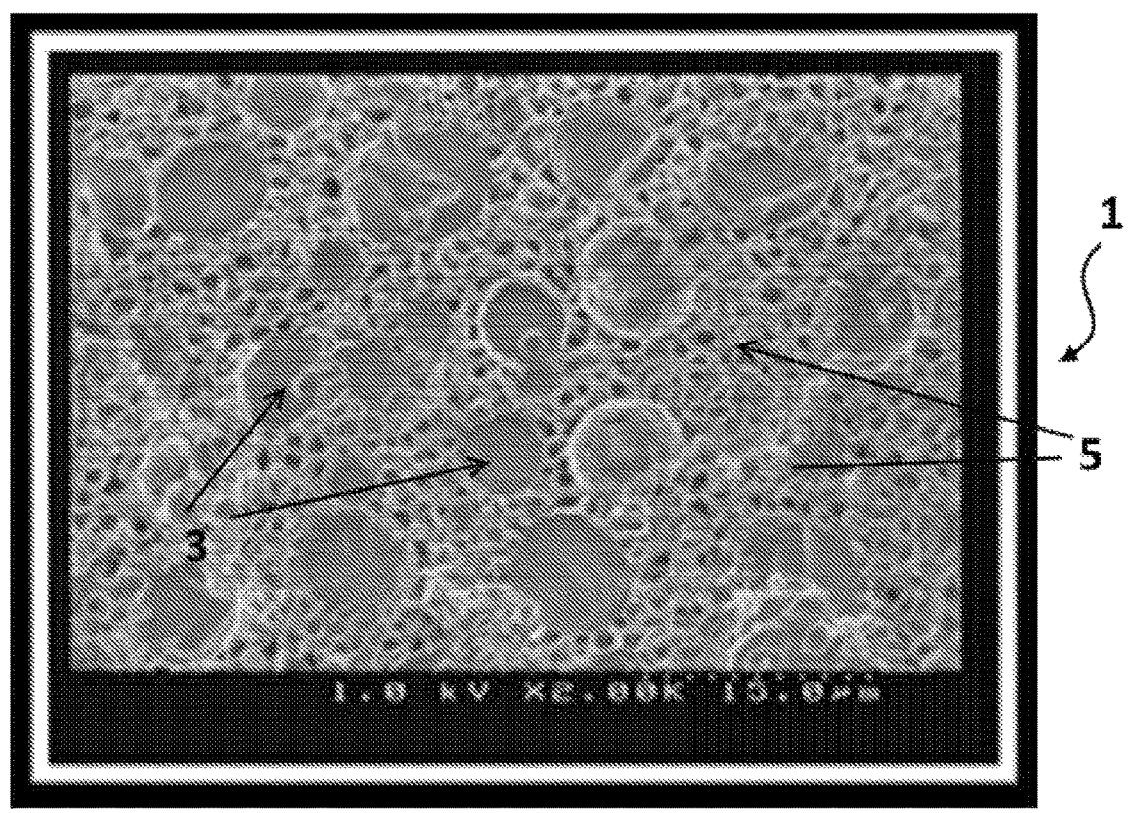
FIG. 1A is a freeze-fracture Scanning Electron Microscopy (SEM) image of homogeneous emulsion droplets surrounded by clay particles, in accordance with a preferred embodiment of the invention.
Figure 1B:
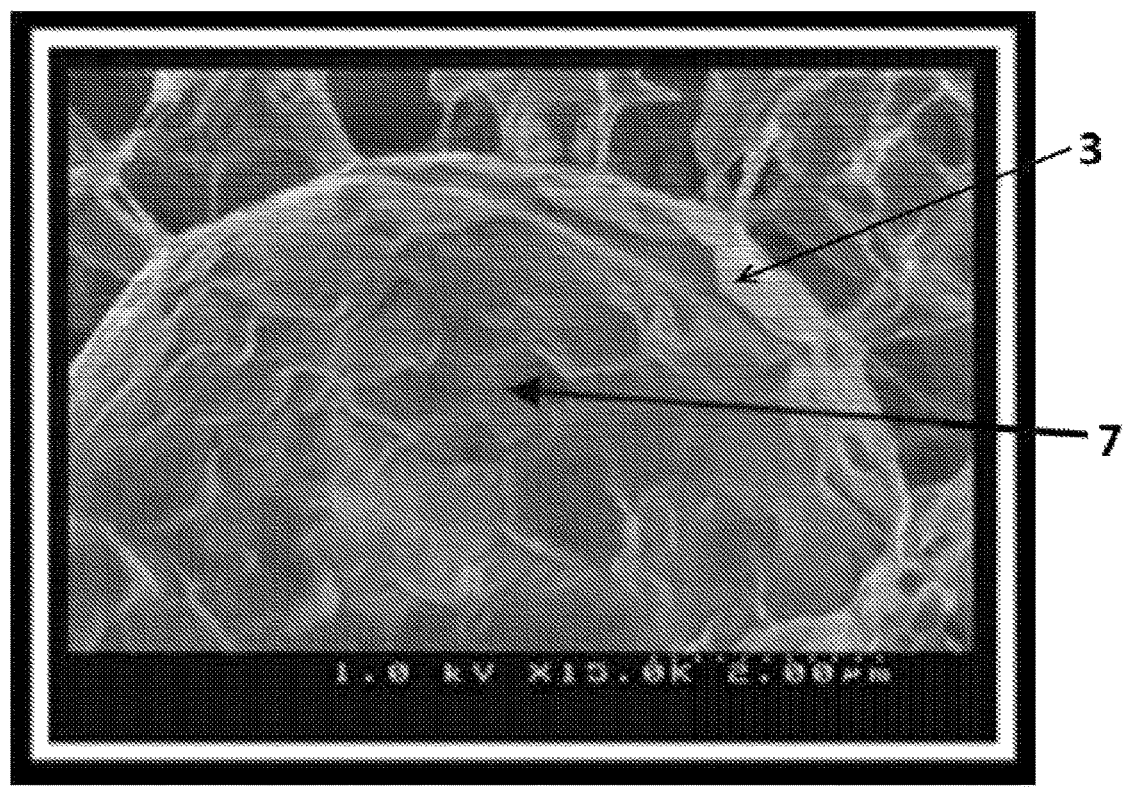
FIG. 1B is an amplified SEM image of FIG. 1A showing fractured oil droplets, non fractured oil droplet and the formation of the network in a continuous phase, in accordance with a preferred embodiment of the invention.

FIG. 1A is a freeze-fracture Scanning Electron Microscopy (SEM) image of an homogeneous Pickering emulsion 1 of droplets 3 surrounded by clay particles 5. FIG. 1B is an amplified SEM image of FIG. 1A showing fractured oil droplets 3-1, non fractured oil droplet 3-2 and the formation of the network in a continuous phase 7.

Figure 2A:
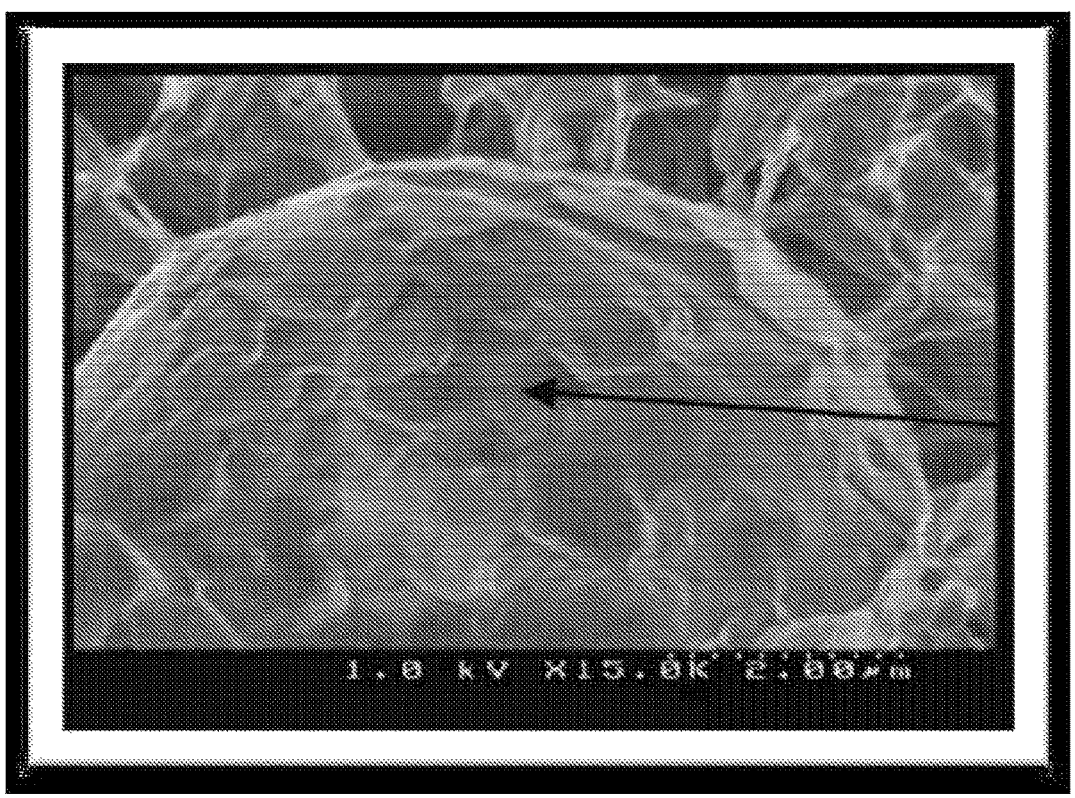
FIG. 2A is a more amplified image of FIG. 1A or 1B, showing an oil droplet covered by clay particle, in accordance with a preferred embodiment of the invention.
Figure 2B:
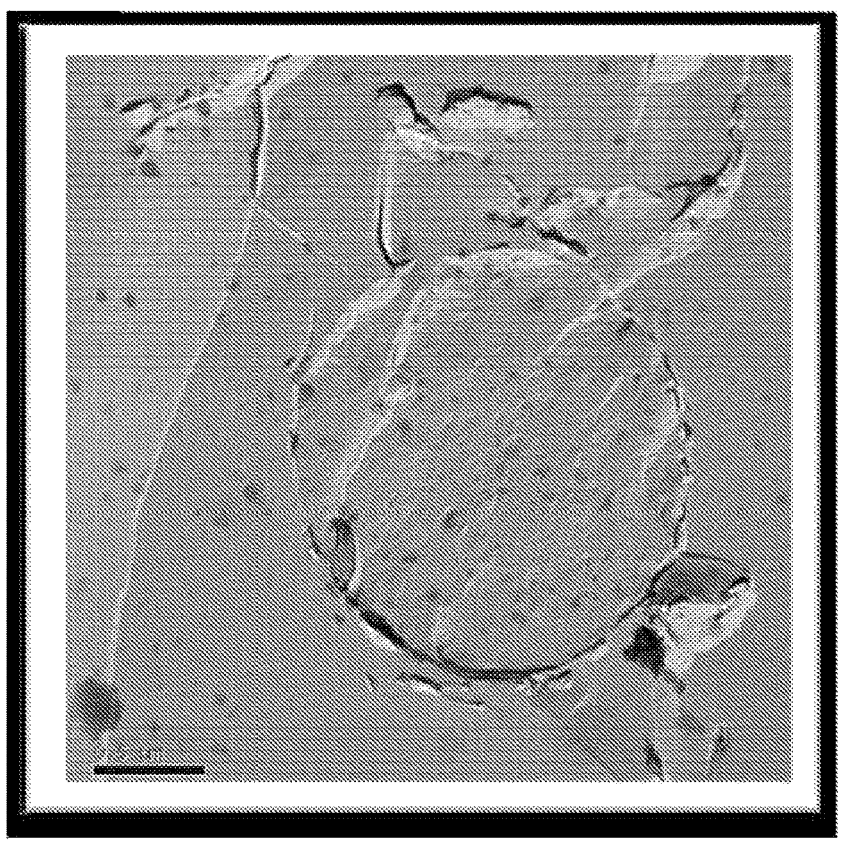
FIG. 2B is a freeze-fractured TEM image showing the adsorption of organic-modified clays at the interface between oil droplets and the water, in accordance with a preferred embodiment of the invention.

In a first step: the emulsion forms a layer preventing the coalescence of oil droplets 3 in the water phase 7. The oil phase is thus completely encapsulated into the mineral structure. FIG. 2A shows the oil droplet 3 covered by clay particles 5.

Figure 3:
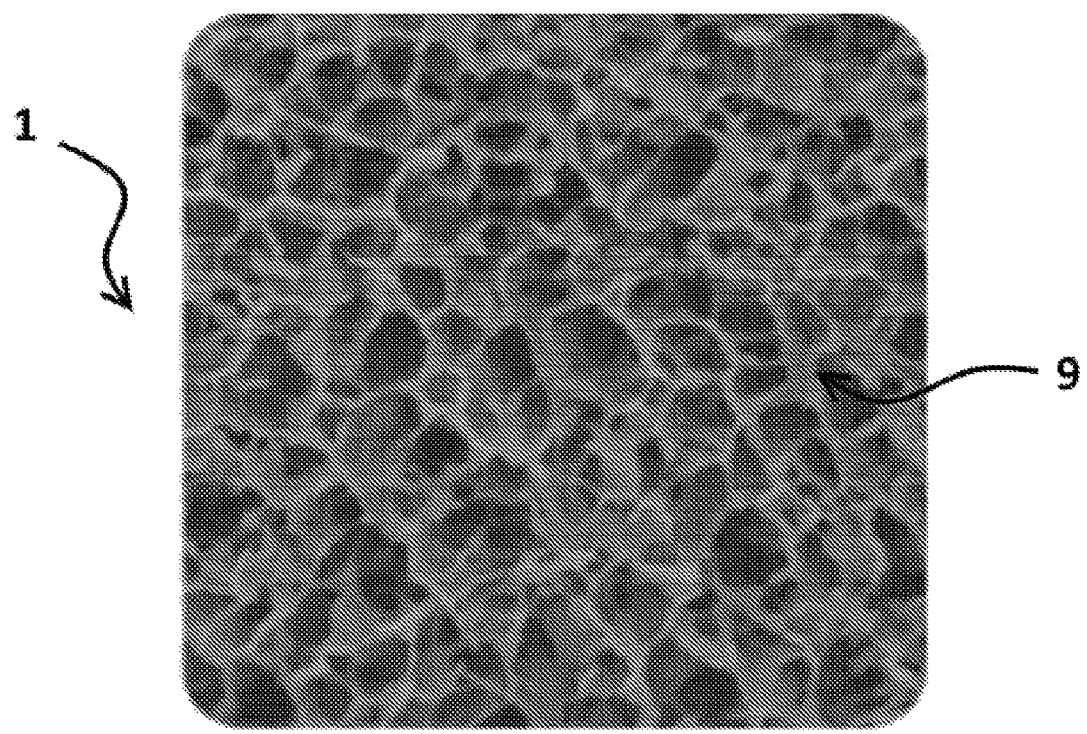
FIG. 3 is a freeze-fracture SEM image of the emulsion with a three-dimensional (3D) network in a continuous phase like a honeycomb structure, in accordance with a preferred embodiment of the invention.

In a second step, and referring to FIG. 3 showing a freeze-fracture SEM image of the emulsion, a three-dimensional (3D) network 9 is formed in a continuous phase like a honeycomb structure. The network formation increases the stability of the emulsion reducing the movement of the discontinuous phase and protects the oil droplets. The stabilization of the water-oil interface prevent the coalescence of the dispersed droplets. Accordingly, there is no need of emulsifier or surfactant in the composition according to the present invention. The composition according to the present invention is therefore free of emulsifier, co-emulsifier or thickening agents normally used in emulsion formulations. The composition allows higher dispersability of the other ingredients, such as but not limited to pigment or active ingredients if any.

The composition in accordance with the present invention can be made by following steps:
a. Adding an amount of organic-modified natural clay to an oil phase;
b. Mixing gently the clay and the oil phase to obtain a first mixture; and
c. Adding gently the first mixture to a water phase under vigorous stirring.

EXAMPLES

Film Forming Compositions

Figure 4:
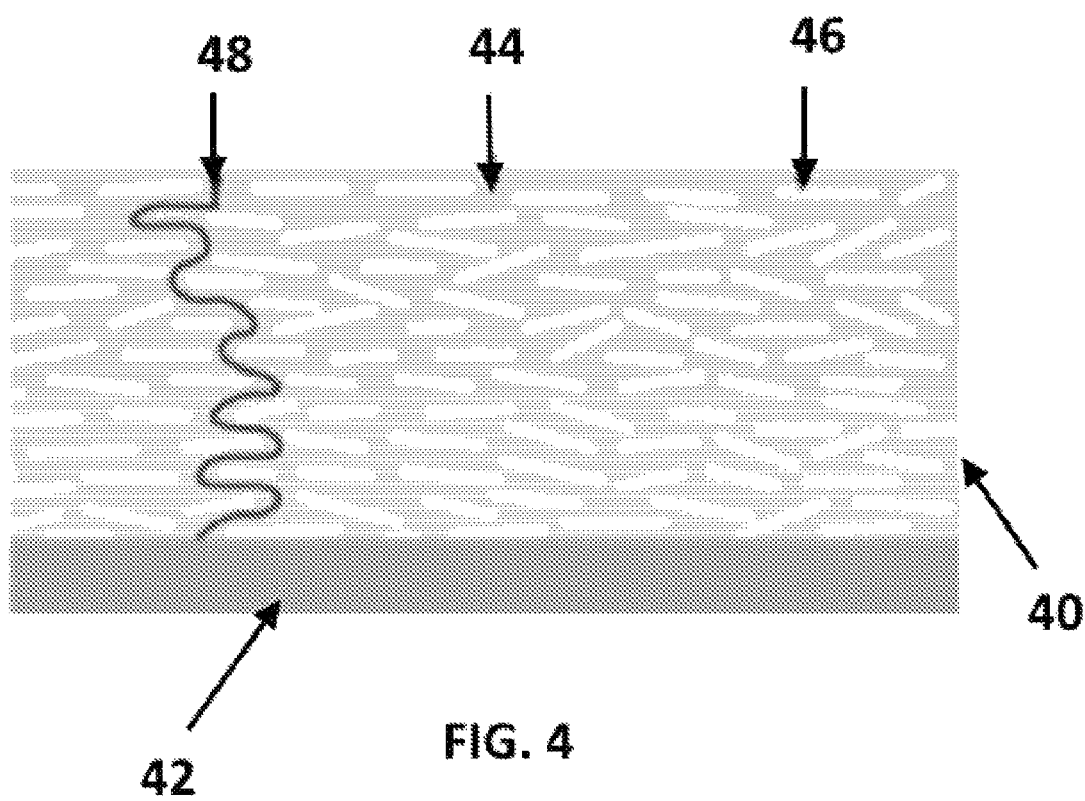
FIG. 4 is a schematic view of the skin covered with a composition in accordance with a preferred embodiment of the invention.

As shown on FIG. 4, the composition in accordance with the invention forms a film 40 on the skin 42. The film comprises an oil and water phase 44 and the 3D network or matrix 46 formed by the organic-modified natural clay, creating as such a tortuous path 48 to reach the skin 40. Once on the skin, the mineral structure like a second skin allows delivering in a controlled manner the oil & water phases thanks to the creation of a labyrinth path. The network formation increases the stability of the emulsion reducing the movement of the discontinuous phase.

In other words, the present invention provides physical interactions between the clay platelets of the Pickering that have collapsed on the human skin to form the film (such like card game). The platelets, as shown on FIG. 4, creates a reservoir effect, or slow delivery system, where the organic molecules of the Pickering formulation must then take a longer path to reach the skin.

Rheological Behavior

FIGS. 5 to 8 are different diagrams showing the rheological properties of the composition according to the present invention under stress or shearing. Structured fluids like pickering emulsion often will not flow unless they have reached a critical stress level called the yield stress, below which the emulsion is "fully" elastic and above which the structure of the emulsion breaks and it flows.

Figure 5:
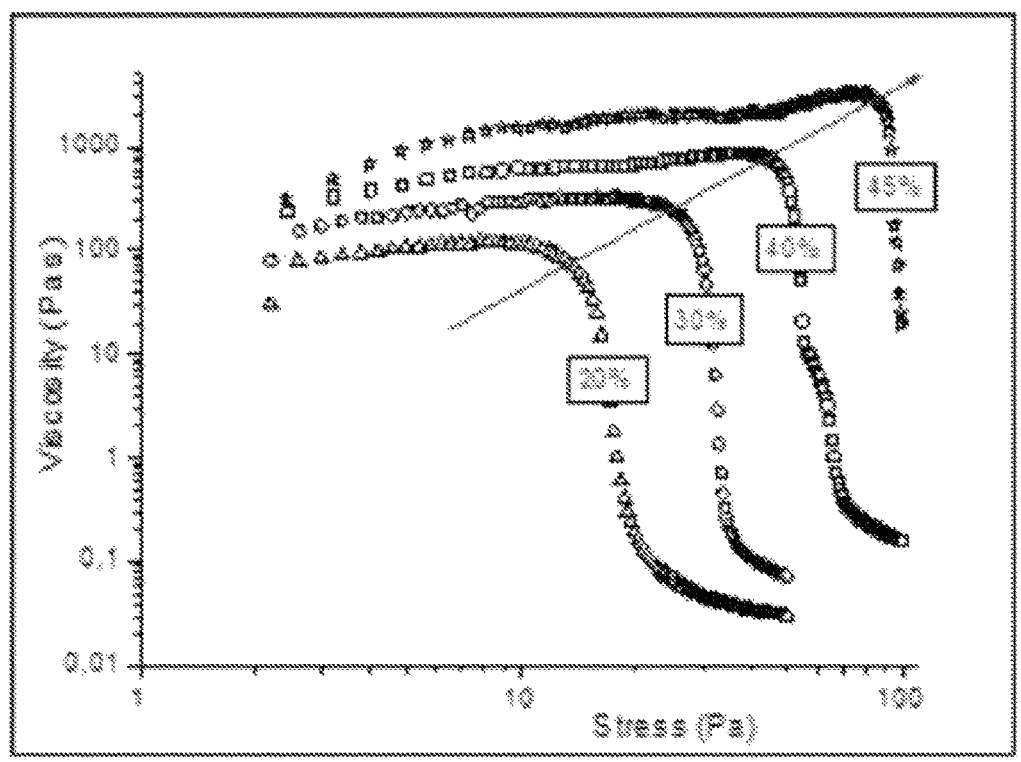
FIG. 5 is diagram showing the viscosity (Pa·s) under stress (Pa) of different composition in accordance with preferred embodiments of the invention for different oil concentrations (20, 30, 40 and 45%)
Figure 6:
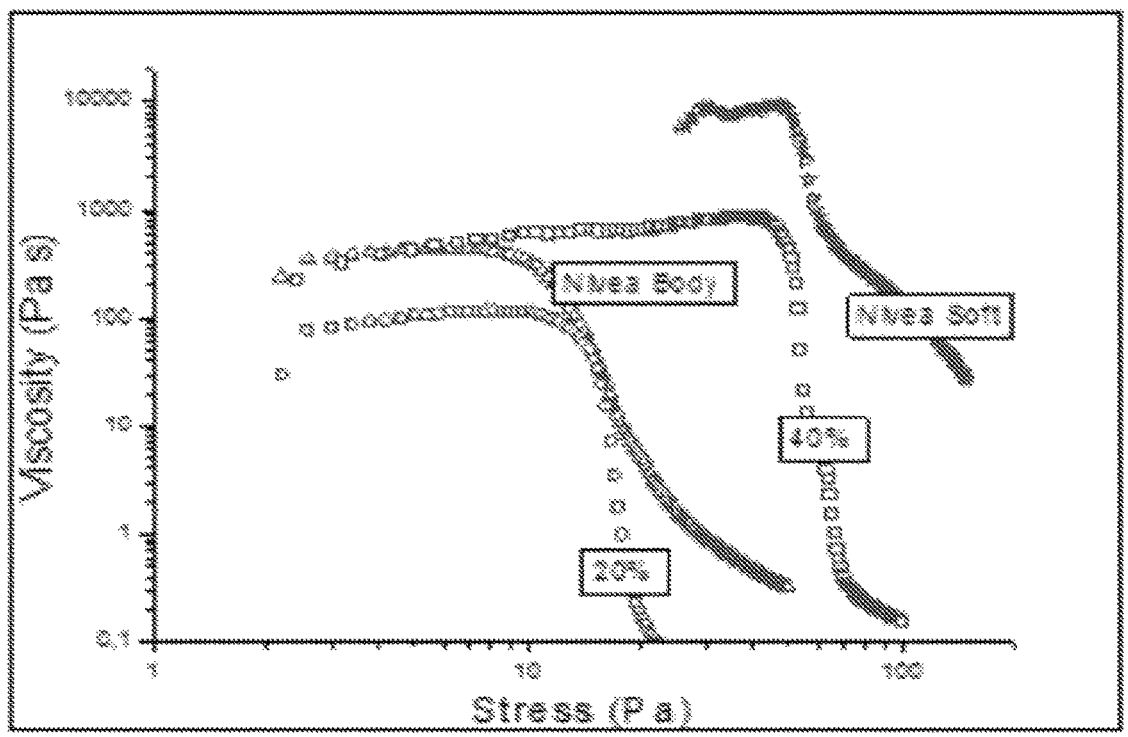
FIG. 6 is diagram showing the viscosity (Pa·s) under stress (Pa) of different composition in accordance with preferred embodiments of the invention for different oil concentrations (20 and 40%) in comparison with commercial emulsions of the prior art.

In FIG. 5, four compositions having different oil concentration of 20, 30, 40 and 45%. There is a linearity of the stress value under which the composition starts to flow. By comparing on FIG. 6 the rheological behaviour of the compositions of the present invention with composition on the market (Nivea Body™ and Nivea Soft™). Even in this absence of emulsifier, the composition of organic-modified natural clay have a rheological behaviour similar to the behaviour of the composition on the market comprising such emulsifier.

Figure 7:
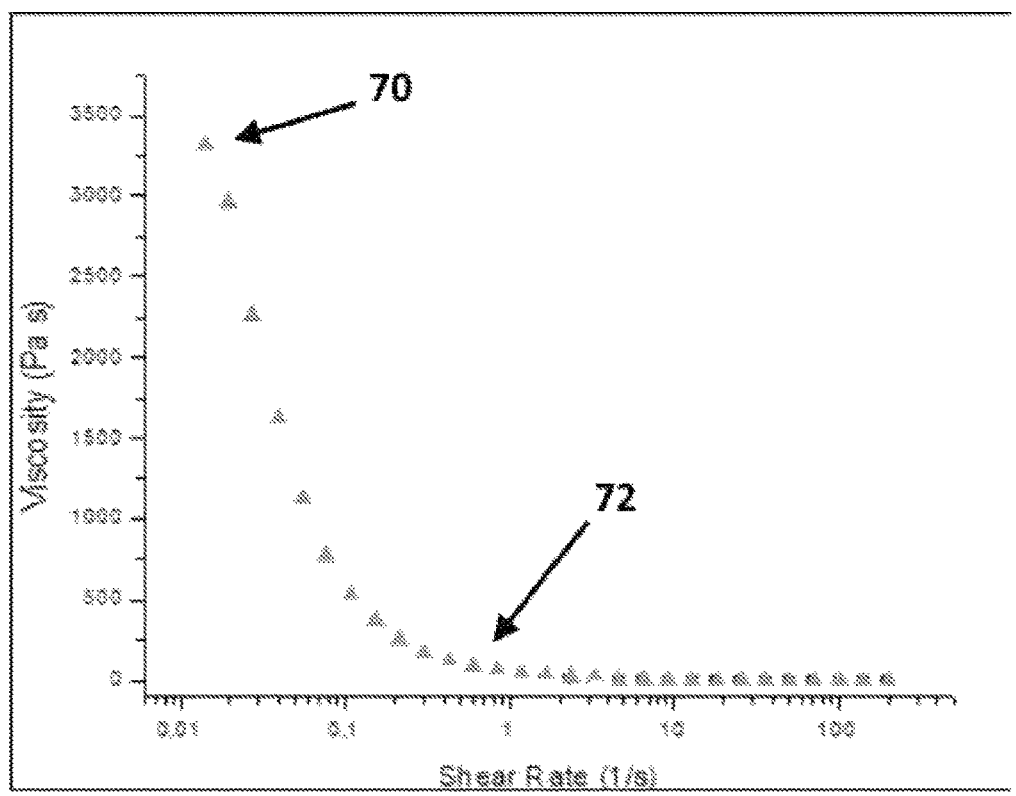
FIG. 7 is diagram showing the viscosity (Pa·s) under shear rate (1/s) for two compositions in accordance with preferred embodiments of the invention.

FIG. 7 is diagram showing the viscosity (Pa·s) under shear rate (1/s) for a composition in accordance with preferred embodiments of the invention. Triangles 70 are for a composition Frametime® Structure CX with a concentration of 5% of modified clay. The data of FIG. 7 shows a normal behaviour under shearing in that the emulsions start to flow under a shearing value 72 comparable with the shearing created by the small forces needed to manually applied the emulsion on the skin by a person. A high viscosity 70 is desirable when removing the cream from the jar and at the start of the application.

Figure 8:
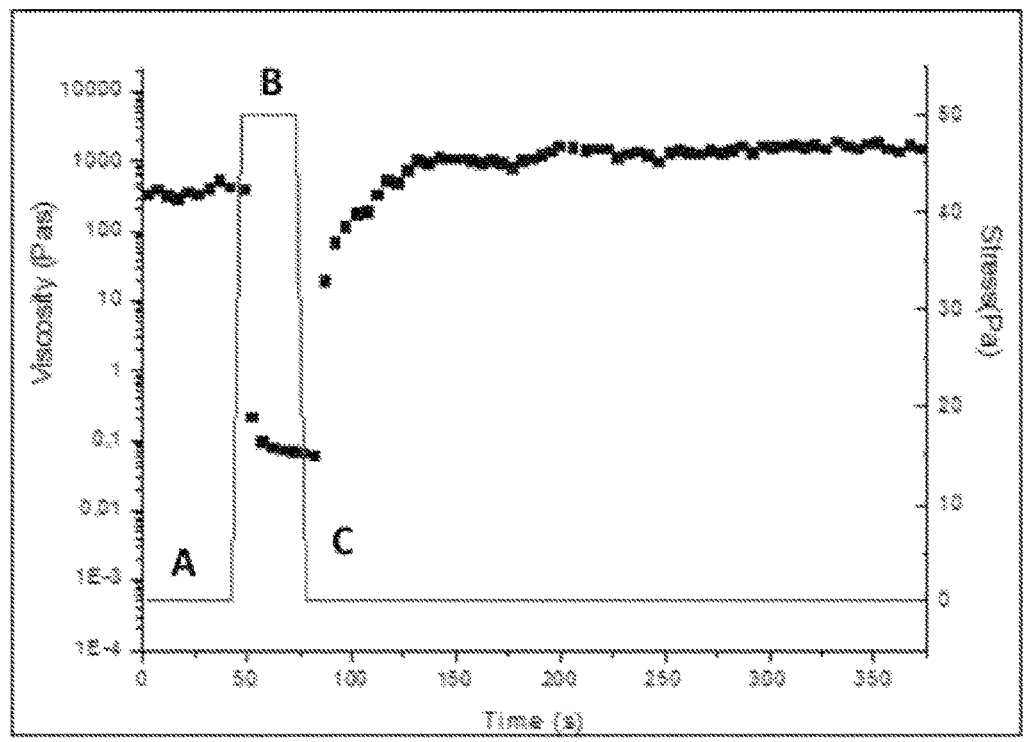
FIG. 8 is diagram showing the viscosity behaviour in time after a stress of a composition in accordance with a preferred embodiment of the invention.
Figure 9A:
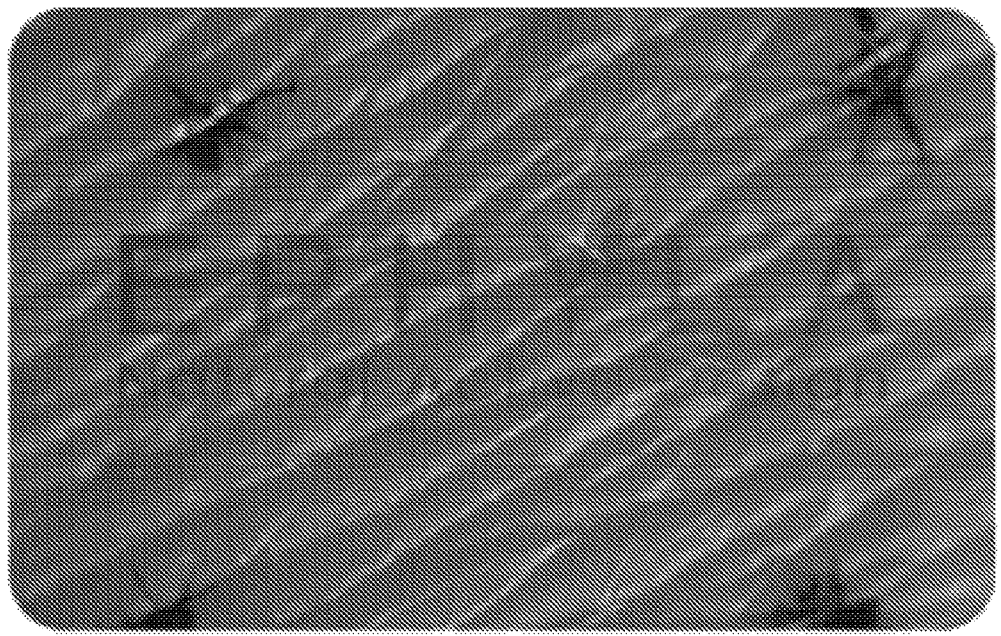
FIGS. 9A and 9B are pictures showing respectively the skin before the application of the composition s in accordance with preferred embodiments of the invention (FIG. 9A), and after the application (FIG. 9B).
Figure 9B:
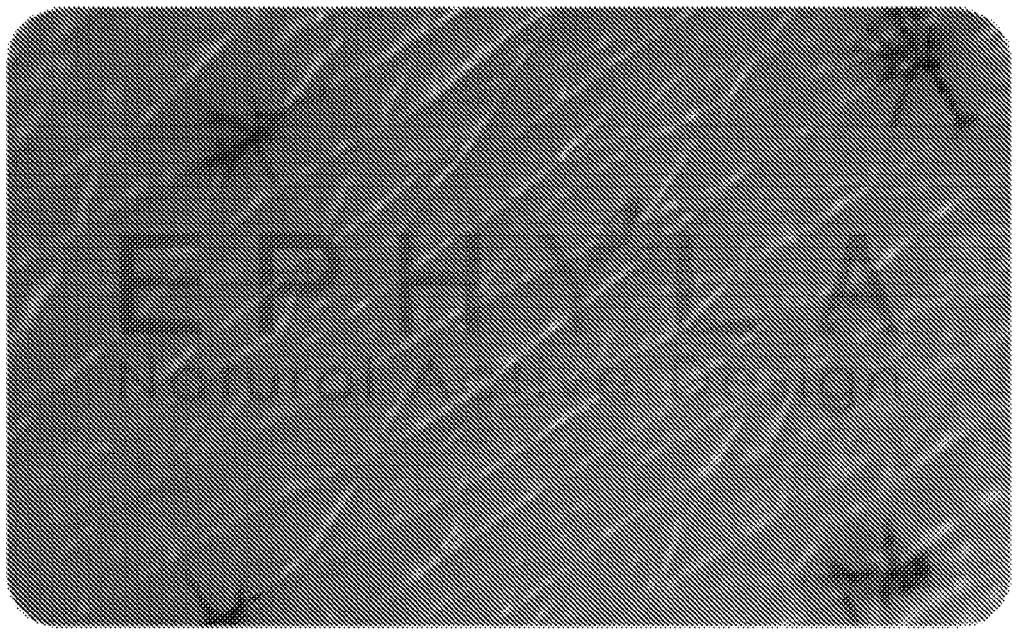

Most cosmetic emulsions are deformed when a small amount is removed for instance from a jar. How quickly the structure of the emulsion is restored can be crucial. FIG. 8 shows the viscosity behaviour in time after a stress of a composition in accordance with a preferred embodiment of the invention. The stress segment A is the composition at rest. The stress segment B shows that the amplitude of the stress is suddenly increased (100-fold over the LVR), corresponding to a breakdown of the structure. The stress segment C shows that the viscosity returns to the initial value of segment A, demonstrating that the structure of the emulsion builds up. The composition according to the present invention has therefore a viscoelastic behaviour perfectly adapted for the making of a cosmetic or pharmaceutical formulation or cream.

Cosmetic Compositions

According to preferred embodiments, table 1 below discloses different examples of formulations that are particularly useful in the making of cosmetic formulations.

TABLE 1

EXAMPLES OF FRAMETIME ® FORMULATIONS

| IN-HOUSE NAME AND GRADES | PRINCIPAL INGREDIENTS | PROPERTIES |
|---|---|---|
| FRAMETIME ® CX | Bentonite; Xanthan gum; and Citric acid | Especially designed for: facial and hand cream, washing creams; opaque shampoos. Frametime ® CX allows to prepare highly rheo-thinning emulsions with unique touch feel and spreading |
| FRAMETIME ® CXG | Bentonite; Xanthan gum; Citric acid; and Sodium stearoyl glutamate* | Frametime ® CX is especially designed for lotions milk like products, as cleansing lotions and body milk. (*) Sodium stearoyl glutamate is a secondary surfactant used as co-emulsifier. |
| FRAMETIME ® CCL | Bentonite; Chitosan; and Lactic acid | Frametime ® CCL is especially designed for creams and hair care products thanks to the film-forming properties. |
| FRAMETIME ® LTX | Sodium magnesium silicate; Xanthan gum; and Citric acid | Frametime ® LTX is especially designed to support the Frametime C grades in order to obtain a cushion effect and a silky touch for make-up and face care applications. |

The above formulations are:
Specially designed to stabilize oil in water emulsions.
Emulsifier free*: primary organic emulsifiers (such as non-ionic or anionic emulsifiers) generally used for cosmetic applications can be irritating for the human skin, especially for sensitive skin and allergenic skins,
Respect of the natural skin's barrier layer: since the formulations do not modify the surface tension of epidermal surface hydrolipid layer.
Biomolecules protection.
Rheological modifier.
Make-Up applications:
  increase pigment dispersibility;
  increase the water proofing effect; and
  increase the soft-focus effect.
Sunscreen applications:
  SPF booster in synergy with mineral-based sunscreen.
Sun Screen Composition According to one preferred embodiment, Table 2 below discloses a sunscreen formulation in accordance with a preferred embodiment of the present invention. Table 3 shows that the sunscreen formulation contains 99% of natural origin ingredients.

TABLE 2

Sunscreen SPF 50 (LXG_FSPF5)

| Supplier | Ingredient | % | Inci Name LXG_FSPF5_F1 |
|---|---|---|---|
| EPHYLA | Frametime CX | 3.30 | Bentonite & Xanthan gum & citric acid |
| NSL | EX81 | 0.70 | Polyglyceryl-8 Oleate |
| NSL | TeresterTricap | 4.00 | Tricaprylin |
| EPHYLA | Desert date oil | 4.00 | Balanites roxburghii seed oil |
| INOLEX | Lexfeel 7 | 3.00 | Neopentyl Glycol Diheptanoate |
| NSL | NS SOLAR DSP | 28.00 | Caprylic/capric triglyceride & Polyglyceryl-3 diisostearate & Mica Titanium dioxide & Zinc oxide |
| MLW | Benzyl alcohol | 1.00 | Benzyl alcohol |
| Masso | Tocopherols mixed | 0.05 | Tocopherols mixed |
| EPHYLA | citric acid | 0.50 | Citric acid |
| | Water | 55.45 | Aqua |
| pH = 4.7 ± 0.3 | | 100.00 | |

TABLE 3

Natural ingredients of Sunscreen SPF 50 (LXG_FSPF5)

| | Sunscreen SPF 50 -INCI List LXG_FSPF5-F1 | |
|---|---|---|
| | Designation | Origin |
| Aqua | Solvent | Natural |
| Caprylic/capric triglyceride & Polyglyceryl-3 diisostearate & Mica & Titanium dioxide & Zinc oxide | Mineral Sunscreen | Natural |
| Balanites roxburghii seed oil | Vegetal oil | Natural |
| Tricaprylin | Vegetal triglyceride | Natural |
| Neopentyl Glycol Diheptanoate | Vegetal ester | Natural |
| Bentonite | Ephyla technology | Natural |

TABLE 3-continued

Natural ingredients of Sunscreen SPF 50 (LXG_FSPF5)

| | Sunscreen SPF 50 -INCI List LXG_FSPF5-F1 | |
|---|---|---|
| | Designation | Origin |
| Benzyl alcohol | Preservative | Chemical |
| Polyglyceryl-8 Oleate | dispersant | Natural |
| Xanthan gum | Gelifying agent | Natural |
| Citric acid | pH adjustor | Natural |
| Tocopherols mixed | Vitamin E | Natural |

Natural components = 99%

This sunscreen has a SPF 50 and does not contain any primary surfactant (just dispersant for premix pigments). The absence of primary surfactant is an important improvement in the field of sunscreen formulations. Indeed, the UVA/UVB filters and/or screens are not stabilised by chemical agents but by a tridimensional system allowing obtaining a physical emulsion (see FIG. 4).

Another advantage of the sunscreen formulation disclosed herewith is that it can be prepared at room temperature by selecting an oil phase that is liquid at room temperature. The process for preparing the sunscreen formulation disclosed herewith comprises at least the following steps:
 a. providing an aqueous phase and an oil phase;
 b. making a pulverulent phase of $TiO_2$ and Frametime®;
 c. dispersing the pulverulent phase of $TiO_2$ and Frametime® into the oil phase, such as by vigorously stirring the oil phase;
 d. homogenizing the water phase in order to solubilise the preservatives;
 e. adding the oil phase into the water phase under fast stirring.

As shown in Table 4 below, the process is advantageous compared to the making of regular emulsion, in that it does not require a lot of energy.

TABLE 4

Comparisons between a regular process and a process in accordance with the present invention:

| Regular process | Process using Frametime ® |
|---|---|
| For the making of 400 kg of emulsion | |
| 40 kW of electricity consumed | 0.4 kW of electricity consumed |
| Large emission of $CO_2$ | Reduced emission of $CO_2$ |
| 2 hours of preparation time | 15-30 minutes of preparation time |
| Use of primary surfactants that can be irritating for the skin | No primary surfactant |

Table 5 below compares the SPF of a tinted sunscreen formulation according to the present invention using Frametime® and a classic tinted sunscreen using standard chemical surfactants. The following results have been obtained by evaluating the SPF in vitro using HelioTest® method no. 1; and evaluating the UVA using HelioTest® method no. 2.

TABLE 5

SFP comparisons:

| References Client | Reference Hélioscience | SPF | UVA Protection | Ratio SPF/UVA |
|---|---|---|---|---|
| Ephyla -UBS Tinted Cream Frametime CX | 3Ubr01-0310 | 5.38 | 3.92 | 1.37 |
| Ephyla -UBS Classic tinted cream | 3Ubr02-0310 | 4.54 | 3.51 | 1.29 |
| Control PMMA 16-18 | 3T0310 | 17.3 | 8.2 | 2.09 |

It is shown in Table 5 that the use of Frametime® allows increasing the SPF of 189.5%, and more particularly the UVA protective indicia of more than 11.5%.

Stretch Mark Reduction

The following clinical study of the formulations disclosed herewith demonstrates the efficiency of the phyllosilicate compositions disclosed herewith.

Clinical Study of Phyllosilicate Compositions:

The objective of this study is to evaluate and compare the in-vivo efficacy of two products reducing the appearance of stretchmarks coded:

SKIN REGENERATOR SGspin
SKIN REGENERATOR SGep

The evaluation is performed using:

MORPHOLOGIC AND COLORIMETRIC ANALYSIS OF STRETCHMARKS ON PHOTOGRAPHS
SELF EVALUATION QUESTIONNAIRE

The study lasts 56 days following the first application of the products. 24 subjects are selected for the study. The subjects selected for this study are healthy females, aged between 19 and 37 years old. These subjects are selected according to the inclusion/non inclusion criteria listed herein after.

Study Protocol

1. Subject Selection:

Spincontrol's subject panel is composed of subjects selected on the basis of a questionnaire filled in on a computer, prior to the study that provides details of their medical history, possible allergies, skin-care and make-up habits, as well as a certain amount of administrative information. The inscriptions are made by a certified beautician.

The selection procedures are elaborated in order to guarantee that the subjects receive all possible information about the aims of the study and the consequences of their participation. This selection procedure includes:

a preliminary interview, during which the following points are explained to the subjects: the study's modalities, its practical considerations, possible payment, as well as any possible cosmetic benefits, inconveniences or potential risks;

the information form which is specific to the study, including all essential information is then read;

the consent form is read, approved, and signed by the subject to substantiate the fact that they freely accept the conditions of the study which has been described to them;

the consent form which was filled in freely and intentionally by the subject after it had been fully explained to them, in the event of any claims for damages, enables them to benefit from the terms of the insurance policies taken out by both the investigator and by the study sponsor as soon as the subject is accepted onto the study by the study manager.

The subject must respect the following conditions: (as well as those already mentioned):

Available for the entire duration of the study;
Motivated to freely participate in the study;
Willing to follow the full product application procedure;
Able to justify a permanent address;
Able to understand the French language: i.e. only French-speaking subject capable of reading the consent documents and able to accept the participation conditions;
Benefiting from Social Security medical cover;
No individual sentenced to imprisonment by a court decision or by an administrative decision, or hospitalized without consent, or admitted in a medical or social establishment, unless the study can be carried out in the conditions defined in the article L1121-6 of the public health code;
No minor (article L1121-7) as well as individual of age benefiting from a legal protection measure or enable to express its consent (article L1121-8) insofar as the study can be carried out in some other manner;

The subjects selected for the study are chosen under the supervision of the investigator and study manager, on the basis of the inclusion/non inclusion criteria listed below.

A selection of 24 subjects is made for this study. The results given include all of the present and assessable subjects at each examination.

1.1. Inclusion Criteria

Standard criteria: Female; Healthy; Between 18 and 45 years of age; Skin at assessed area is healthy (free of psoriasis, eczema, erythema, oedema, scars, wounds or lesions).

Specific Criteria:

Having a Caucasian skin type;
With at least two stretchmarks of recent appearance (less than 12 months), inflammatory (pink to red-purple), bilateral and identical degree of inflammation (same intensity of color);
Stretchmarks appeared in one of the following circumstances: pregnancy, after violent muscle exercises, after large and rapid change in weight (loss or gain);
For subjects who appeared stretchmarks during pregnancy:
    in absence of breastfeeding: having given birth for at least one month;
    With lactation: have stopped breastfeeding for at least one month.

1.2 Non-Inclusion Criteria:

Standard Criteria

Failing to meet the aforementioned inclusion criteria;
Being in remanence, at the beginning of the study, on the studied area(s), following another cosmetic, dermatological, or medical test;
Having undergone any major surgery in the previous year.
Having undergone plastic surgery on the studied area(s).
Taking part in another study liable to interfere with this study.
Being diabetic.
Being asthmatic.
Having participated in skin or peri-ocular tolerance testing in the past two weeks and/or in sensitisation trials in the past four months.
The refusal to give their assent by signing the consent form.
Being pregnant (unless the study can be carried out according to the conditions defined in the article L1121-5 of the public health code).
Having sun-tanned skin.
Having changed their cosmetic habits in the 14 days preceding the start of the study on the concerned area(s).
Having cutaneous hypersensitivity or a skin allergy to cosmetic products.
Following a chronic medicinal treatment comprising any of the following products taken orally: aspirin-based products, anti-inflammatory, anti-histamines, corticotherapy (the only medication permitted is Paracetamol™).
Having applied a cosmetic product (except the usual cleanser) to the studied area(s) the day of measurement.
Refusing to follow the restrictions below during the study:
    Do not take part in another study liable to interfere with this study.
    Do not become pregnant during the study.
    Do not expose their selves to artificial UV light and/or to the sun during the study.
    Do not change their cosmetic habits during the study on the concerned area(s).
    Do not follow a chronic medicinal treatment comprising any of the following products taken orally: aspirin-based products, anti-inflammatories, anti-histamines, corticotherapy.
    The days of measurements no cosmetic product, including the tested product to the studied area, must be used (except the usual cleanser).
    During the study, the application of any other cosmetic product to the studied area(s) is proscribed (only the usual cleanser is accepted).

Specific Criteria

E Having a Cushing's syndrome (abnormal increase in cortisol);
Having used cosmetics anti-stretchmarks in the two weeks preceding the start of the study;
Having made beauty treatments (exfoliation, scrub, massage, self-tanner . . . ) in the week preceding the start of the study;
Having applied a topical retinoid in the month preceding the start of the study;
Having used the sessions of laser, LED photomodulation, mechanical or chemical peel (dermabrasion), cosmetic surgery to treated stretchmarks evaluated;
Refusing to follow the following restrictions below during the study:
    Do not perform exfoliation, scrub, massage of skin and not apply self-tanning product;
    Do not carry treatment of stretchmarks (cosmetics and microdermabrasion kits, topical medications, laser, peeling . . . );
    Do not start an intense sporting activity (bodybuilding . . . );
    Do not have a large and fast weight variation (gain or loss);
    The days of measurements do not wear tight clothing or underwear before the acquisition (the skin should not be marked by clothing and underwear).
    Keep a strict photo-protection of the evaluated areas 2. The Products:

| SKIN REGENERATOR | Constituent form: | Packaging | Capacity of |
|---|---|---|---|
| SGspin (Table 6) | Emulsion | Airless | 50 ml |

-continued

| SKIN REGENERATOR | Constituent form: | Packaging | Capacity of |
|---|---|---|---|
| SGep (Table 7) | Emulsion | Airless | 50 ml |

According to one preferred embodiment, it is disclosed in Table 6 below the formulation of the skin regenerator SGspin.

TABLE 6

Example of skin regenerator formulation SGspin (placebo cream):

| COMMERCIAL NAME | INCI NAME | % M.A. | % REELS |
|---|---|---|---|
| FRAMETIME CX | Bentonite & Xanthan gum & Citric acid | 100 | 3 |
| Gomme Xanthane | Xanthan gum | 100 | 0.4 |
| Eumulgin SG | Sodium stearoyl glutamate | 100 | 0.5 |
| BIO SUNFLOWER OIL | Helianthus annuus seed oil | 100 | 22 |
| AMS LEUCIDAL | Leuconostoc/Radish root ferment filtrate | 100 | 0.5 |
| AMINAT G | Glycerin & Arginine HCl | 100 | 0.8 |
| Sodium Benzoate | Sodium benzoate | 100 | 0.5 |
| Bioxan SFT 50 | Tocopherol mixed | 100 | 0.2 |
| Skin Regenerator* | Bentonite & Borojoa patinoi extract & Ulva lactuca extract | 100 | 0 |
| Water | Aqua | 100 | 72.1 |
| * 90% Reverteam et 10% Revertime | pH = 5.5 |  | 100 |

According to one other preferred embodiment, it is disclosed in Table 7 below the formulation of the skin regenerator SGep or Regeneryl®.

TABLE 7

Example of skin regenerator formulation SGep:

| COMMERCIAL NAME | INCI NAME | % M.A. | % REELS |
|---|---|---|---|
| FRAMETIME ® CX | (Bentonite & Xanthan gum & Citric acid) | 100 | 2 |
| Xanthan gum | Xanthan gum | 100 | 0.4 |
| Eumulgin SG (Secondary or co-emulsifier) | Sodium stearoyl glutamate | 100 | 0.5 |
| Sunflower oil | Helianthus annuus seed oil | 100 | 22 |
| AMS LEUCIDAL | Leuconostoc/Radish root ferment filtrate | 100 | 0.5 |
| AMINAT G | Glycerin & Arginine HCl | 100 | 0.8 |
| Sodium benzoate | Sodium benzoate | 100 | 0.5 |
| Bioxan SFT 50 | Tocopherol mixed | 100 | 0.2 |
| Skin Regenerator (Regeneryl ®) 90% Reverteam et 10% Revertime | Bentonite & Borojoa patinoi extract & Ulva lactuca extract | 100 | 1 |
| Water | Aqua | 100 | 72.1 |
| pH 5.5 |  |  | 100 |

2.1 Presentation of the Products:

The test product(s) is supplied free of charge by the study sponsor. The study sponsor is in charge of product manufacturing and packaging. He/She is responsible for product identification, purity determination, composition, innocuousness, and any other characteristics of each product to be tested prior to the beginning of the study.

The study sponsor is responsible for supplying the exact amount of product needed to carry out the test(s). For this study, the study sponsor agrees to supply:

The appropriate quantity of the product required to treat all of the subjects;

A sufficient quantity of the product for any additional subjects participating in the study;

One product unit per reference and per batch to be retained in the sample cabinet of SPINCONTROL.

Products are stored in an ambient temperature away from light. At the end of the study, the products used by the volunteers or the left over products can be sent back to the promoter if he has asked for it on the document attached to the quotation or by mail. On the other hand, the investigator proceeds to eliminate the remaining products according to the method of their choice described in their procedures. The cost of the products destruction by the investigator is charged to the promoter.

2.2 Product Application:

| SKIN REGEN-ERATOR | Application area(s) | Frequency of application | Application duration | Conservation |
|---|---|---|---|---|
| SGspin | One stretchmark chosen at T0 | 2 times/day | 56 days | At room temperature |
| SGep | Another stretchmark chosen at T0 | 2 times/day | 56 days | At room temperature |

Quantities of application should correspond to normal conditions of use. Massage gently so as to form a thin and light film to the skin surface 3 Study Design:

This study is carried out as a "double blind test". Neither the participating subjects nor the investigator are aware of the type of product being applied throughout the study; only the sponsor is aware of the nature of the products.

This is a comparative study in which the results obtained at one treated area by one of the products are compared with those obtained at another treated area with the other product.

The subjects serve as their own reference and results obtained at various assessment times are compared with those obtained at T0.

4. Study Procedures:

4.1 Analysis of the Colour of the Stretchmarks by Means of Digital Photographs 4.1.1 Acquisition of Source Data Principle: This technique consists of obtaining high resolution photographs of the stretchmarks, in completely reproducible lighting conditions, in cross polarized light. The acquisitions are carried out with a high resolution camera. The lens used is a Nikkor™ 60 mm equipped with a filter. Lighting is provided by two flash lights. The flash heads are fitted with filter slots to hold polarising gel (HN32 Sarelec, France). The filter on the lens is oriented to a 90° angle in comparison with the filter on the flashes. The polarised light, emitted by the flashes and reflected by the stretchmarks at the moment the photo is taken, is "cut" by the filter. These reflections do not appear on the photograph when it is obtained enabling a better visualisation of the changes in skin colour on the various studied areas.

Acquisition Methodology:

Environmental conditions: The evaluation is carried out in a dark room under a controlled temperature (21±1° C.) and relative hygrometry (45±5%).

Subject: A 20-minute period of acclimatisation in the air-conditioned room is respected. The position of the subjects depends of the localisation of the stretchmarks. The stretchmarks can be localized on the stomach, thighs, buttocks, hips or breasts.

Measurements: An acquisition of the treated is made at each time of the kinetics. The visualisation of the initial digital photograph (T0) at Tn ensures a good repositioning of the subject.

Figure 10:
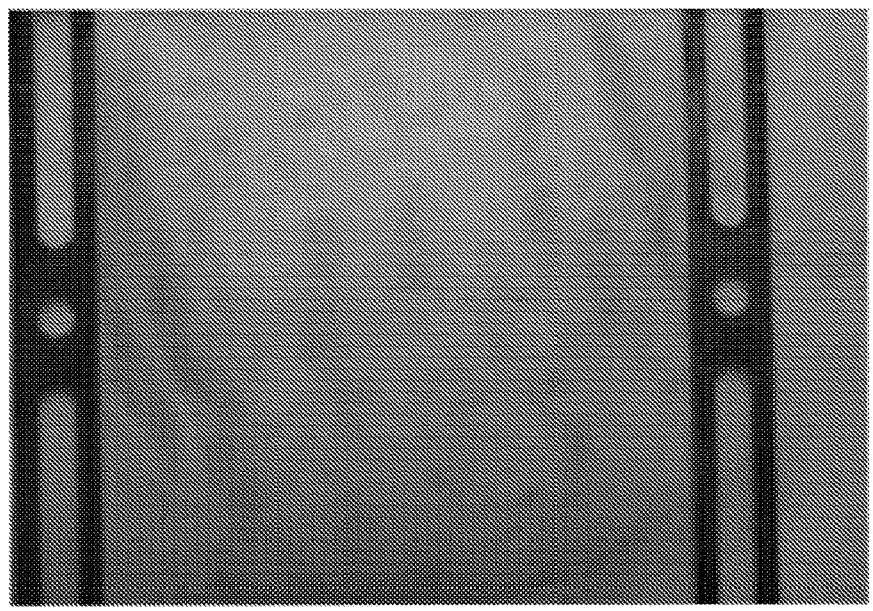
FIG. 10 is a picture of stretchmarks on human skin (stomach).

FIG. 10 shows stretchmarks of human skin taken on the stomach.

4.1.1 Morphology of Stretch Marks

Figure 11A:
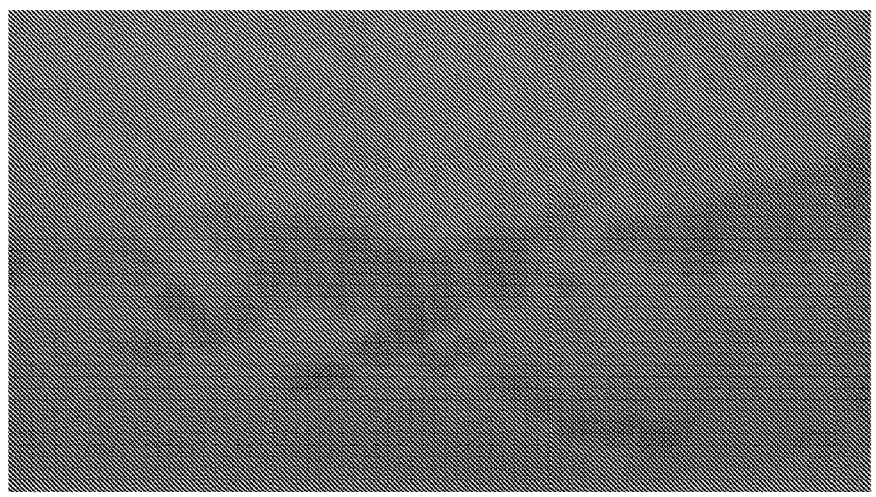
FIGS. 11A and 11B are pictures of stretchmarks on human skin using specific software.
Figure 11B:
Figure 12:
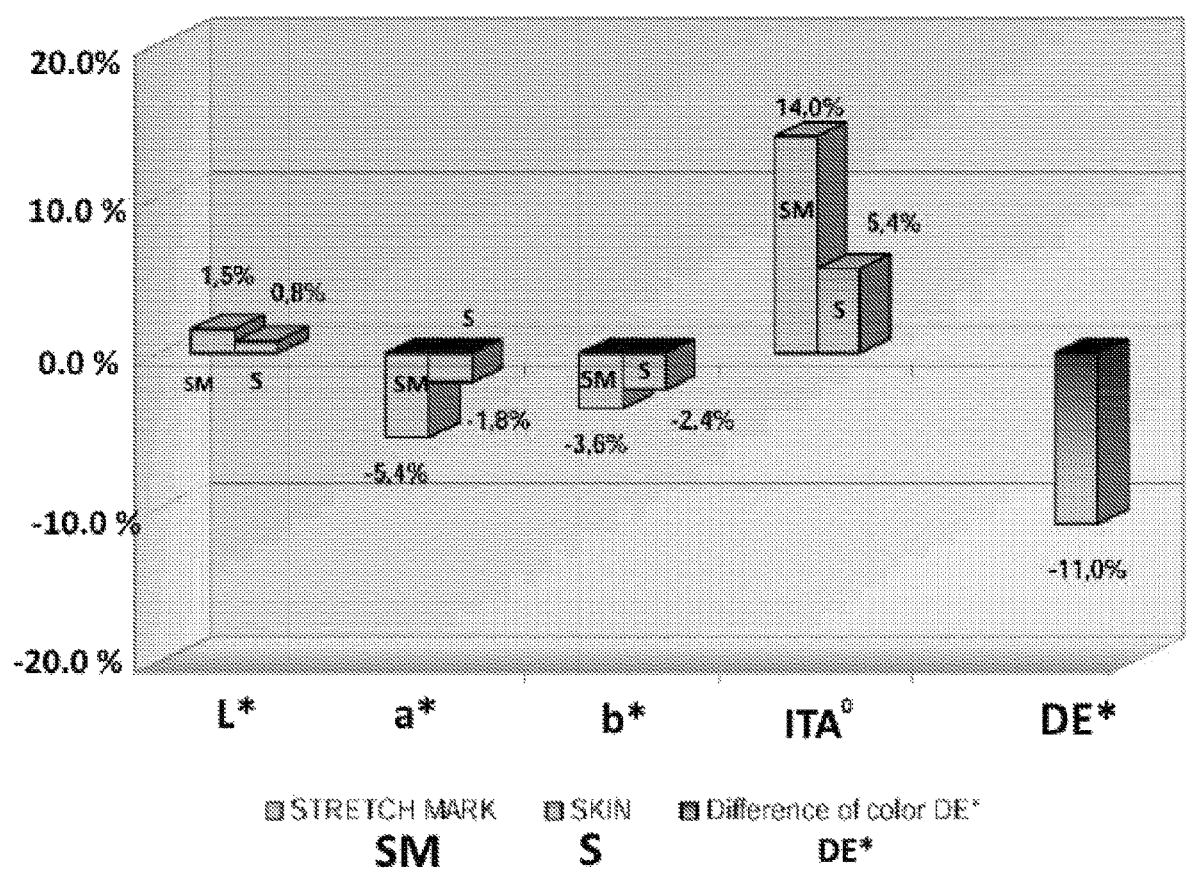
FIG. 12 is a graphic of the evolution of the parameters of the colorimetric analysis on digital photographs after 56 days of application of the product named. Skin Regenrataor SGspin.
Figure 13:
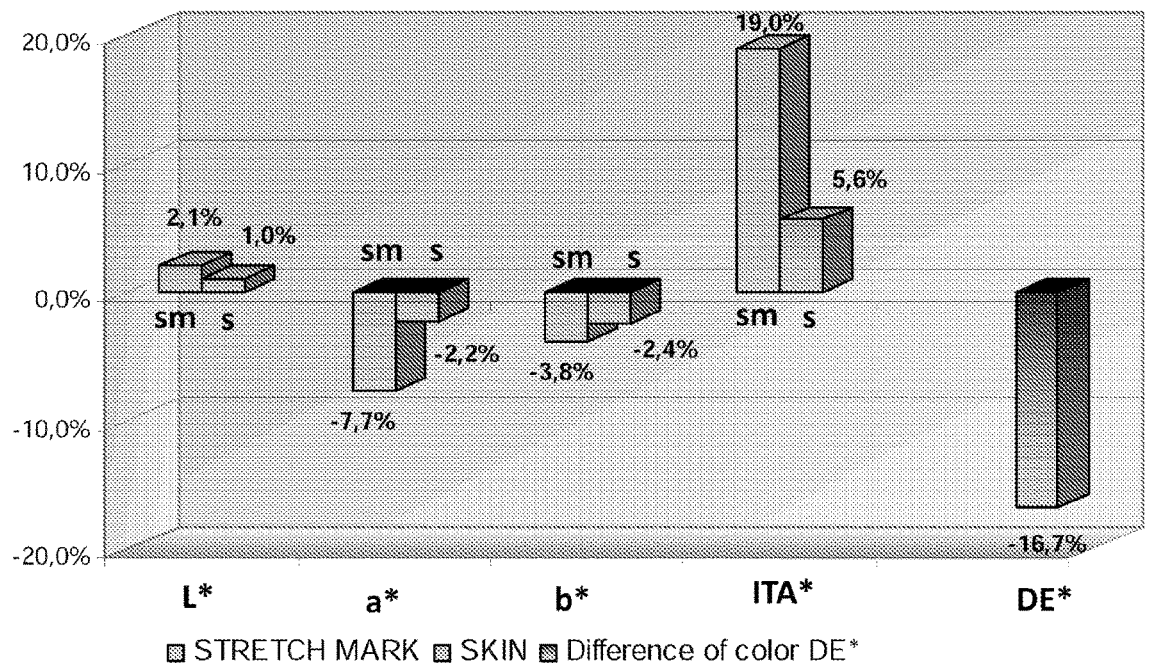
FIG. 13 is a graphic of the evolution of the parameters of the colorimetric analysis on digital photographs after 56 days of application of the product named. Skin Regenrataor SGep.

Parameters: Photographs of FIGS. 11A and 11B are processed using specific software developed by Spincontrol. After digitization, subtraction of background noise and threshold, the following parameter is determined:

Area of the studied stretch marks (pixel).

This analysis is carried out for the stretchmarks treated by each product.

Exploitation:

4.1.3 Colorimetry of Stretchmarks.

Treatment software and methodology: This analysis is carried out on the same pictures as those used for the morphologic analysis. On each photograph, two regions of interest are defined: the stretch mark and a zone of normal skin (without stretch mark). The use of dedicated software allows us to determine L*, a* and b* parameters from the RGB components of the digital image, on the stretch marks.

Parameters: This method enables us to determine the following parameters, on studied areas:

L*: brightness a*: chromaticity coordinate representing the balance between red and green b*: chromaticity coordinate representing the balance between yellow and blue ITA°=Arctg[(L*−50)/b*]. (180/π): individual typological angle $\Delta E = \sqrt{(\Delta L^2 + \Delta a^2 + \Delta b^2)}$: difference in colour between two given areas (the area with a stretch mark and the area with normal skin).

Exploitation: The results analysis is based on the most important parameter of colour which is ΔE: the comparison in time of this parameter allows determining the effect of the tested product on the skin colour of the stretch mark.

4.2 Self Evaluation Questionnaire 4.2.1 Acquisition of Source Data

Principe: The subjects have to fill in a questionnaire in order to evaluate the overall opinion and their attitude towards the effectiveness of the products being tested. The questionnaires are carried out in accordance with the promoter (see appendix 3 of the study protocol)

Acquisition Methodology:

Measures: The questionnaires are filled in Spincontrol office. The subjects are in front of a mirror and fill in the questionnaire individually without any extrinsic influences (others volunteers, results of technical measurements). The filling of the questionnaire is performed under control of a technician who checks the acquisition according to an operating method 4.2.2 Treatment of Source Data Software and methodology: The questionnaires are carried on and exploited with dedicated software reachable from an Internet browser. The raw data are treated and analysed with Excel (Microsoft).

4.3 Examination Schedule

The effects of the products are evaluated over a 56-day period. The scheduled measurement procedures are as follows:

Preinclusion:
Checking of the inclusion/non inclusion criteria;
Clinical observation and description of the quality of the skin at the measuring areas;

At T0 Before the Application of the Product:
Acclimatisation
Acknowledgement, reading and signature of the consent form;
Checking of the inclusion/non inclusion criteria;
Clinical observation and description of the quality of the skin at the measuring areas;
Weighing of each subject
Location of the measuring areas and drawing up of the skin-marking maps;
Photographs of the stretchmarks
Weighing and distribution of the test products and distribution of the information form.

At T+56 Days
Acclimatisation
Weighing of each subject
Checking of the proscriptions and restrictions;
Weighing of the test products
Discussion about the subject's tolerance towards the product(s);
Clinical observation of the quality of the skin at the measuring areas;
Positioning of the skin-marking map;
Self evaluation questionnaires
Photographs of the stretchmarks
End of test-product application. Subjects are indemnified.

Comment: the questionnaires are filled in by the subjects before carrying out any measurements to avoid influencing their judgment about the test product(s).

4.4. Data Analysis and Statistics 4.4.1. Data Analysis of Technical Data

The results include:

Raw values for each subject at each examination.

Differences, in relation to T0 for each subject during the study (Tn−T0).

Means, medians, maximum, minimum and standard deviations of the raw values and of the differences in relation to T0 obtained by the entire panel.

Variations, in relation to T0 expressed as a percentage calculated from the mean values.

Numbers and percentages of subjects presenting an improvement.

Comparison in time, for each product: Verification of the normality of the distributions using Shapiro-Wilk test, threshold at 1%, for each product. The statistical analysis of the evolution of the measured parameters during the study for each product is performed using the Student test (normality of distributions checked) or with the Wilcoxon test (normality of the distributions rejected). The significance threshold is fixed at 5%.

Comparison of the two products: Verification of the normality of the distributions using Shapiro-Wilk test, threshold at 1%, for the comparison of the two products at T0 and at Tn−T0. The statistical comparison of the two products, at T0 and on the differences (Tn−T0), for each of the measured parameters, is performed with the Student test (normality of distributions checked) or the Wilcoxon test (normality of the distributions rejected). The significance threshold is fixed at 5%.

4.4.2 Data Analysis of Self-Evaluation

The analysis involves establishing frequency tables that take into account the number of responses and calculate the frequency of the different possible answers (given as percentage) to each qualitative question. For each question, results are shown in tabular form (number of individuals and frequency). To evaluate the efficacy and the appreciation of the products for each item, two percentages Z1 and Z2 are calculated as follows:

Z1=favourable opinion(Ex: "Completely agree"+ "Somewhat agree")

Z2=unfavourable opinion(Ex: "Completely disagree"+"Somewhat disagree")

The statistical difference in frequencies (%) between favourable and unfavourable opinions is evaluated using the Chi-squared test at 5%. The statistical comparison between the two products is realized using a KHI-DEUX test of Mac Nemar at 5%.

5. Results

Section 5.1 to 5.8 of the results of the clinical trials and studies are presented as an Annex starting on page 28 of the present description/specification.

5. Results 5.1 Deviations from the Study Protocol

➤ Respect of the Study Schedule

Two subjects (subject no 1 DEDCH and subject no 21 PE CGE) came on the $2^{nd}$ of December instead of on the $5^{th}$ of December for the last visit. They applied the product during 53 days instead of 56 days.

Considering the duration of the study, these deviations have been considered as minor and the data of these subjects has been exploited in the results.

5.2 Absences

Subject no 13 (CHAVA) and subject no 17 (GSCAU) were absent at T+56 days.

T0 data for these subjects has not been exploited so they have been excluded from the study panel.

5.3 Non Exploitable Data for Technical Reasons

Colorimetric and Morphologic Analysis of the Stretchmarks

Subject no 9 (NADJ1): data non exploited at all the examination times

Subject no 16 (BO244): data non exploited at all the examination times

Subject no 22 (RENV4): data non exploited at all the examination times 5.4 Population Considered in the Expression of the Results At T0, 24 subjects were recruited.

Considering the information previously mentioned in the paragraphs 5.1 to 5.3, which led to "non exploited data" for several subjects, the number of subjects considered in the expression of the results, at each examination time, and for each technique, is presented in the following table:

| Techniques | Times | |
|---|---|---|
| | T0 | T + 56 days |
| MORPHOLOGIC AND COLORIMETRIC ANALYSIS OF STRETCHMARKS ON PHOTOGRAPHS | 19 | 19 |
| SELF EVALUATION QUESTIONNAIRE | | 22 |

5.5 Description of the Exploited Panel

The exploited panel consisted of 22 women aged between 19 and 37 years old (Mean age: 26 years old, see detail in appendix 1), of a Caucasian skin type, with at least two stretchmarks of recent appearance (less than 12 months), inflammatory (pink to red-purple), bilateral and identical degree of inflammation (same intensity of color).

5.6 Follow Up of the Weight

The detailed results (individual results and statistics) of the follow-up of the weight are presented in appendix 1

The following table summarises the weight follow-up on the exploited panel after 56 days of study.

| | Weight Raw values (Ka) | | Weight Evolution (Tn − T0) (Kg) |
|---|---|---|---|
| | T0 | T + 56 days | (T + 56 days − T0) |
| Mean | 72.4 | 72.3 | −0.1 |
| Standard deviation | 11.6 | 11.9 | 2.0 |
| Median | 69.0 | 71.2 | −0.1 |
| Maximum | 100.3 | 100.9 | 4.7 |
| Minimum | 58.1 | 56.7 | −3.9 |
| Number of subjects | 22 | 22 | 22 |

The statistical analysis does not show any significant variation of the weight between T0 and T+56 days (p=7.44E-01 (Student t test for paired sample at 5%, after checking the normality of the distributions by the Shapiro-Wilk test at 1%).

Therefore, the weight has no influence on the study results.

5.7 Colorimetric Analysis of the Stretchmarks on Photographs

The detailed results of the colorimetric analysis of the stretchmarks and the corresponding statistics are presented in appendix 2

The studied parameters are:

L*: brightness a*: chromaticity coordinate representing the balance between red and green b*: chromaticity coordinate representing the balance between yellow and blue ITA°=Arctg[(L*−50)/b*]. (180/π): individual typological angle $\Delta E = \sqrt{(\Delta L^2 + \Delta a^2 + \Delta b^2)}$: difference in colour between two given areas (the area with a stretch mark and the area with normal skin).

For each product, the parameters L*, a*, b*, ITA° are calculated for the stretchmarks and the skin around the stretchmarks.

The statistical analysis is carried out on the parameters a* and ΔE

For an effect of the product, a decrease of these parameters must be shown.

5.7.1 Observed Results on Each Stretchmark

➤ Skin Regenerator SGspin

→Raw Values

The following table summarises the means and standard deviations of the raw values of the colorimetric parameters observed on the stretchmarks treated by the product Skin regenerator SGspin at T0 and T+56 days, as well as the corresponding statistical results for the evolution in time (Student test, two-tailed for paired groups at 5%, after checking the normality of the distributions by a Shapiro-Wilk test at 1%).

|  |  | RAW VALUES | | | |
|---|---|---|---|---|---|
|  |  | STRETCH MARK | | SKIN | |
|  |  | T0 | T + 56 days | T0 | T + 56 days |
| L* | Mean | 57.68 | 58.57 | 60.99 | 61.47 |
|  | Standard deviation | 2.25 | 2.21 | 1.68 | 1.89 |
| a* | Mean | 16.85 | 15.93 | 11.88 | 11.66 |
|  | Standard deviation | 3.30 | 3.47 | 2.36 | 2.52 |
|  | Significant at 5% (T0 vs Tn) |  | No |  | No |
|  | p= |  | 6.86E-02 |  | 3.14E-01 |
|  | Test |  | Student t test |  | Student t test |
| b* | Mean | 17.37 | 16.75 | 17.41 | 16.99 |
|  | Standard deviation | 4.21 | 3.95 | 2.57 | 2.46 |
| ITA° | Mean | 24.63 | 28.09 | 32.53 | 34.28 |
|  | Standard deviation | 8.71 | 8.50 | 6.09 | 6.58 |

|  |  | T0 | T + 56 days |
|---|---|---|---|
| Difference of color DE* | Mean | 6.48 | 5.77 |
|  | Standard deviation | 2.98 | 2.79 |
|  | Significant at 5% (T0 vs Tn) |  | No |
|  | p= |  | 1.26E-01 |
|  | Test |  | Student t test |

→Evolutions (Tn−T0)

The following table presents the means and the standard deviations of the evolutions (Tn−T0) of the colorimetric parameters observed on the treated stretchmark.

Product Ref: Skin Regenerator SGspin

|  |  | EVOLUTION OF THE PARAMETERS (Tn − T0) | |
|---|---|---|---|
|  |  | STRETCH MARK T + 56 days − T0 | SKIN T + 56 days − T0 |
| L* | Mean | 0.89 | 0.48 |
|  | Standard deviation | 1.75 | 1.29 |
| a* | Mean | −0.92 | −0.22 |
|  | Standard deviation | 2.06 | 0.92 |
| b* | Mean | −0.63 | −0.42 |
|  | Standard deviation | 1.14 | 1.00 |
| ITA° | Mean | 3.45 | 1.75 |
|  | Standard deviation | 5.31 | 3.77 |

|  |  | T + 56 days − T0 |
|---|---|---|
| Difference of color DE* | Mean | −0.71 |
|  | Standard deviation | 1.93 |

→Variations (Tn−T0)/T0(%)

The following table summarises the average percentages of the variation (Tn−T0)/T0 of the colorimetric parameters observed on the treated stretchmark, calculated from the average values.

Product Ref: Skin Regenerator SGspin

|  | VARIATIONS IN PERCENTAGE (%)* | |
|---|---|---|
|  | STRETCH MARK (T + 56 days − T0)/T0 | SKIN (T + 56 days − T0)/T0 |
| L* | 1.5% | 0.8% |
| a* | −5.4% | −1.8% |
| b* | −3.6% | −2.4% |
| ITA° | 14.0% | 5.4% |

|  | (T + 56 days − T0)/T0 |
|---|---|
| Difference of color DE* | −11.0% |

*calculated on the mean values

→Analysis

No statistical variation in the colour of the stretchmark is observed after 56 days of application of the product Skin Regenerator SGspin.

To be noted, a decrease in the a* parameter in limit of significance is observed (p=6.86E-02; −5.4% on average on the whole panel)

→Raw Values

The following table summarises the means and standard deviations of the raw values of the colorimetric parameters observed on the stretchmarks treated by the product Skin regenerator SGep at T0 and T+56 days, as well as the corresponding statistical results for the evolution in time (Student test, two-tailed for paired groups at 5%, after checking the normality of the distributions by a Shapiro-Wilk test at 1%).

|  |  | RAW VALUES | | | |
|---|---|---|---|---|---|
|  |  | STRETCH MARK | | SKIN | |
|  |  | T0 | T + 56 days | T0 | T + 56 days |
| L* | Mean | 57.17 | 58.35 | 61.22 | 61.84 |
|  | Standard deviation | 2.44 | 1.95 | 1.56 | 1.39 |
| a* | Mean | 17.56 | 16.21 | 11.91 | 11.65 |
|  | Standard deviation | 3.36 | 2.84 | 2.33 | 2.72 |
|  | Significant at 5% (T0 vs Tn) |  | Yes |  | No |
|  | p= |  | 1.64E-03 |  | 2.28E-01 |
|  | Test |  | Student t test |  | Student t test |
| b* | Mean | 16.91 | 16.21 | 16.87 | 16.47 |
|  | Standard deviation | 3.56 | 3.21 | 2.75 | 2.73 |
| ITA° | Mean | 23.12 | 27.51 | 33.96 | 35.88 |
|  | Standard deviation | 8.15 | 6.61 | 5.55 | 4.71 |

|  |  | T0 | T + 56 days |
|---|---|---|---|
| Difference of color DE* | Mean | 7.24 | 6.04 |
|  | Standard deviation | 3.04 | 2.19 |
|  | Significant at 5% (T0 vs Tn) |  | Yes |
|  | p= |  | 3.91E-03 |
|  | Test |  | Student t test |

→Evolutions (Tn−T0)

The following table presents the means and the standard deviations of the evolutions (Tn−T0) of the colorimetric parameters observed on the treated stretchmark.

Product Ref: Skin Regenerator SGep

|  |  | EVOLUTION OF THE PARAMETERS (Tn − T0) | |
|---|---|---|---|
|  |  | STRETCH MARK T + 56 days − T0 | SKIN T + 56 days − T0 |
| L* | Mean | 1.18 | 0.62 |
|  | Standard deviation | 1.32 | 1.00 |
| a | Mean | −1.35 | −0.26 |
|  | Standard deviation | 1.59 | 0.91 |

-continued

|  |  |  |  |
|---|---|---|---|
| b* | Mean | −0.64 | −0.40 |
|  | Standard deviation | 1.23 | 0.98 |
| ITA° | Mean | 4.39 | 1.92 |
|  | Standard deviation | 5.10 | 3.15 |

|  |  | T + 56 days − T0 |
|---|---|---|
| Difference of color DE* | Mean | −1.21 |
|  | Standard deviation | 1.59 |

→Variations (Tn−T0)/T0(%)

The following table summarises the average percentages of the variation (Tn−T0)/T0 of the colorimetric parameters observed on the treated stretchmark, calculated from the average values.

Product Ref: Skin Regenerator SGep

| | VARIATIONS IN PERCENTAGE (%)* | |
|---|---|---|
|  | STRETCHMARK (T + 56 days − T0)/T0 | SKIN (T + 56 days − T0)/T0 |
| L* | 2.1% | 1.0% |
| a* | −7.7% | −2.2% |
| b* | −3.8% | −2.4% |
| ITA° | 19.0% | 5.6% |

|  | (T + 56 days − T0)/T0 |
|---|---|
| Difference of color DE* | −16.7% |

*calculated on the mean values

→Analysis

The statistical analysis shows significant decreases in the a* parameter on the stretchmark and in the ΔE parameter after 56 days of application: respectively −7.7% and −16.7% on average on the whole panel.

5.7.2 Comparison of Both Products

➢ Comparison at T0

The following tables present the statistical results on the comparison of the colorimetric parameters, observed between both stretchmarks at T0 (Student test, two-tailed for paired groups at 5%, after checking the normality of the distributions by a Shapiro-Wilk test at 1%).

Comparison at T0: Product Ref: Skin Regenerator SGep Versus Product Ref: Skin Regenerator SGspin

| | | COMPARSION AT T0 | |
|---|---|---|---|
|  |  | STRETCHMARK | SKIN |
| a* | Significant at 5% | No | No |
|  | p= | 2.86E−01 | 9.24E−01 |
|  | Test | Student t test (two-tailed) | Student t test (two-tailed) |
| Difference of color DE* | Significant at 5% | No |  |
|  | p= | 2.85E−01 |  |
|  | Test | Student t test (two-tailed) |  |

→Analysis

No significant difference between both stretchmarks is noted at T0 for the a* and ΔE parameters. The two stretchmarks are therefore comparable.

➢ Comparison of Both Stretchmarks at T+56 Days (from the Evolutions (Tn−T0))

The following tables present the statistical results for the comparison of the colorimetric parameters observed between both stretchmarks on the evolutions (Tn−T0) (Student test, two-tailed for paired groups at 5%, after checking the normality of the distributions by a Shapiro-Wilk test at 1%).

Comparison from the Difference (Tn−T0): Product Ref: Skin Regenerator SGep Versus Product Ref: Skin Regenerator SGep

| | | COMPARISON FROM THE DIFFERENCES (Tn − T0) | |
|---|---|---|---|
|  |  | STRETCH MARK | SKIN |
| a* | Significant at 5% | No | No |
|  | p= | 4.14E−01 | 8.32E−01 |
|  | Test | Student t test (two-tailed) | Student t test (two-tailed) |
| Difference of color DE* | Significant at 5% | No |  |
|  | p= | 3.85E−01 |  |
|  | Test | Student t test (two-tailed) |  |

→Analysis

No significant difference of evolution is shown at T+56 days between both stretchmarks for the a* and ΔE parameters.

5.8 Morphologic Analysis of the Stretchmarks on Photographs

The detailed results of the morphologic analysis of the stretchmarks and the corresponding statistics are presented in appendix 3

The studied parameter is:

Area of the studied stretch marks (pixel)

5.8.1 Observed Results on Each Stretchmark

➢ Skin Regenerator SGspin

→Raw Values

The following table summarises the means and standard deviations of the raw values of the morphologic parameters observed on the stretchmarks treated by the product Skin regenerator SGspin at T0 and T+56 days, as well as the corresponding statistical results for the evolution in time (Wilcoxon test, two-tailed for paired groups at 5%, after checking the normality of the distributions by a Shapiro-Wilk test at 1%).

Skin Regerenator SGspin

| | | RAW VALUES | |
|---|---|---|---|
|  |  | T0 | T + 56 days |
| Area (pixels$^2$) | Mean | 9925 | 7763 |
|  | Standard deviation | 9065 | 7342 |
|  | T0 vs Tn significant at 5% |  | Yes |
|  | p= |  | <0.001 |
|  | Test |  | Wilcoxon |

→Evolutions (Tn−T0)

The following table presents the means and the standard deviations of the evolutions (Tn−T0) of the morphologic parameters observed on the treated stretchmark.

Skin Regenerator SGspin

|  |  | EVOLUTION OF THE PARAMETERS (Tn – T0) T + 56 days – T0 |
|---|---|---|
| Area (pixels$^2$) | Mean | −2162 |
|  | Standard deviation | 3061 |

→Variations (Tn−T0)/T0(%)

The following table summarises the average percentages of the variation (Tn−T0)/T0 of the morphologic parameters observed on the treated stretchmarks, calculated from the average values.

Skin Regenerator SGspin

|  | Variations in percentages (T + 56 days − T0)/T0 |
|---|---|
| Area | −21.8% |

→Analysis

A significant decrease in the area of the stretchmark is observed after 56 days of application of the product Skin Regenerator SGspin: −21.8% on average on the whole panel.

➢ Skin Regenerator SGep
→Raw Values

The following table summarises the means and standard deviations of the raw values of the morphologic parameters observed on the stretchmarks treated by the product Skin regenerator SGep at T0 and T+56 days, as well as the corresponding statistical results for the evolution in time (Wilcoxon test, two-tailed for paired groups at 5%, after checking the normality of the distributions by a Shapiro-Wilk test at 1%).

Skin Regenerator SGep

|  |  | RAW VALUES | |
|---|---|---|---|
|  |  | T0 | T + 56 days |
| Area (pixels$^2$) | Mean | 6789 | 5431 |
|  | Standard deviation | 4901 | 4071 |
|  | T0 vs Tn significant at 5% |  | Yes |
|  | p= |  | <0.001 |
|  | Test |  | Wilcoxon |

→Evolutions (Tn−T0)

The following table presents the means and the standard deviations of the evolutions (Tn-TO) of the morphologic parameters observed on the treated stretchmark.

Skin Regenerator SGep

|  |  | EVOLUTION OF THE PARAMETERS (Tn – T0) T + 56 days – T0 |
|---|---|---|
| Area (pixels$^2$) | Mean | −1359 |
|  | Standard deviation | 1731 |

→Variations (Tn−T0)/T0(%)

The following table summarises the average percentages of the variation (Tn−T0)/T0 of the morphologic parameters observed on the treated stretchmarks, calculated from the average values.

Skin Regenerator SGep

|  | Variations in percentages (T + 56 days − T0)/T0 |
|---|---|
| Area | −20.0% |

→Analysis

A significant decrease in the area of the stretchmark is observed after 56 day of application of the product Skin Regenerator SGep: −20.0% on average on the whole panel.

Figure 14:
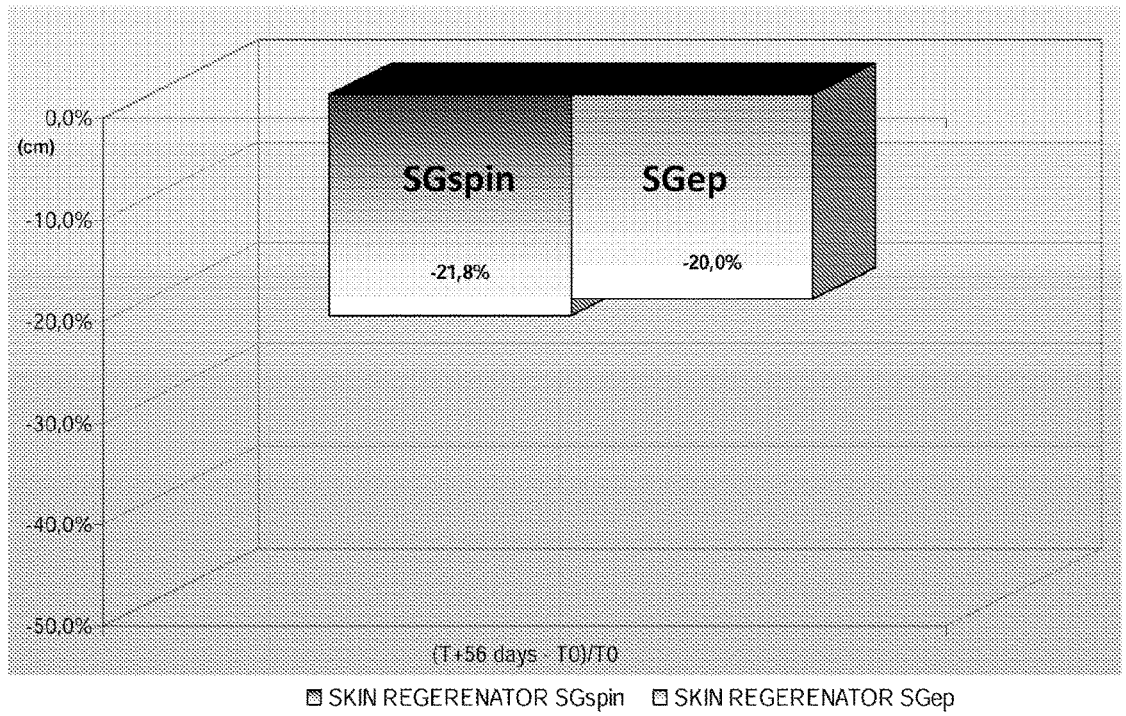
FIG. 14 is a graphic of the evolution of the stretchmarks after 56 days of application of the product named Skin Regenrataor SGspin and Skin Regenrataor SGep.

→Graphic Representation on FIG. 14.

5.8.2 Comparison of Both Products

➢ Comparison at T0

The following table presents the statistical results on the comparison of the morphologic parameters, observed between both stretchmarks at T0 (Wilcoxon test, two-tailed for paired groups at 5%, after checking the normality of the distributions by a Shapiro-Wilk test at 1%).

Comparison at T0: Skin Regenerator SGspin Versus SKIN Regenerator SGep

|  |  | COMPARISON AT T0 |
|---|---|---|
| Area | Significant at 5% | No |
|  | p= | 4.41E−01 |
|  | Test | Wilcoxon |

→Analysis

No significant difference between both stretchmarks is noted at T0 for the area of the stretch marks The two stretchmarks are therefore comparable.

➢ Comparison of Both Stretchmarks at T+56 Days (from the Evolutions (Tn−T0))

The following table presents the statistical results for the comparison of the morphologic parameters observed between both stretchmarks on the evolutions (Tn−T0) (Student test, two-tailed for paired groups at 5%, after checking the normality of the distributions by a Shapiro-Wilk test at 1%).

Comparison from the Differences (Tn−T0): Skin Regenerator SGspin Versus Skin Regenerator SGep

|  |  | COMPARISON FROM THE DIFFERENCES (Tn – T0) T + 56 days – T0 |
|---|---|---|
| Area | significant at 5% | No |
|  | p= | 3.37E−01 |
|  | Test | Student |

→Analysis

No significant difference of evolution of the area of the stretchmark is shown at T+56 days between both products.

5.9 Results of the Self-Assessment Questionnaire:

The following table summarises the agreement percentages recorded for each suggested item after 56 days for each product, as well as their statistical significance evaluated using Chi-squared test at 5%.

5.9.1 Table of results

|  | Skin regenerator SGspin | | Skin regenerator SGep | |
|---|---|---|---|---|
| Subjective Efficacity | % Agreement | Sign. (5%) | % Agreement | Sign. (5%) |
| 1 Your skin is softer | 100 | Yes | 100 | Yes |
| 2 Your skin is more homogeneous | 86 | Yes | 86 | Yes |
| 3 Your skin is firmer | 50 | No | 68 | No |
| 4 Your skin is moisturized | 100 | Yes | 100 | Yes |
| 5 Your skin is more elastic | 68 | No | 59 | No |
| 6 Your stretchmarks are thinner | 64 | No | 45 | No |
| 7 Your stretchmarks are less apparent | 77 | Yes | 68 | No |
| 8 Your stretchmarks have less relief | 82 | Yes | 68 | No |
| 9 Your stretchmarks are less colourful | 91 | Yes | 82 | Yes |
| 10 The length of your stretchmark has decreased | 59 | No | 50 | No |
| 11 The roughness of the skin due to stretchmarks is attenuated | 86 | Yes | 86 | Yes |
| 12 Your skin is softer | 86 | Yes | 86 | Yes |
| 13 Your skin is more homogeneous | 73 | Yes | 77 | Yes |
| 14 Your skin is finner | 36 | No | 50 | No |
| 15 Your skin is moisturized | 91 | Yes | 86 | Yes |
| 16 Your skin is more elastic | 100 | Yes | 100 | Yes |

Subjective efficacy: Concerning the subjective efficacy, the volunteers recognised favorably for both products the following items on the skin property:

your skin is softer (100% of agreement);
your skin is moisturised (100% of agreement);
your skin aspect is more homogenous (86% of agreement).

The volunteers recognised also for both products an effect on the stretchmarks with the items:

your stretchmarks are less colourful (respectively 91% and 82% of agreement for the product skin regenerator SGspin and the product skin regenerator SGep);
the roughness of the skin due to the stretchmarks is attenuated (86% of agreement).

For the product SGspin, t20 more items are significantly validated:

your stretchmarks are less apparent (77% of agreement);
your stretchmarks have less relief (82% of agreement).

Cosmetic qualities: Concerning the cosmetic qualities, the same 4 items out of 5 are recognised for both products with percentages going from 73% to 100% for the product skin regenerator SGspin and from 77% to 100% for the product skin regenerator SGep.

6. Discussion and Conclusion

In our experimental conditions, the twice daily application of the products Skin Regenerator SGspin and Skin Regenerator SGep (on one stretchmark chosen at T0 for each product), for 56 consecutive days, by a panel of 22 women between 19 and 37 years of age, of a Caucasian skin type, with at least two stretchmarks of recent appearance (less than 12 months), inflammatory (pink to red-purple), bilateral and identical degree of inflammation (same intensity of color), leads to the following results:

Colorimetric Analysis of the Stretchmarks on Photographs

A significant decrease in the $a^*$ and $\Delta E$ parameters for the stretchmarks treated by the product skin regenerator SGep, respectively −7.7% and −16.7% on average on the whole panel, is demonstrated after 56 days of application, whereas no significant variation is observed for the product skin regenerator SGspin.

These results traduce for the product skin regenerator SGep a decrease in the redness of the stretchmarks and a decrease in the difference of colour between the skin and the stretchmarks.

No significant difference of evolution of the colorimetric parameters is observed between both products.

Morphologic Analysis of the Stretchmarks on Photographs

A significant decrease in the stretchmarks area is demonstrated after 56 days of study for the product skin regenerator SGspin and skin regenerator SGep. (Respectively −21.8% and −20.0% on average on the whole panel). No significant difference of evolution is observed between both products after 56 days of application Self Assessment Questionnaire Concerning the subjective efficacy, the volunteers recognised for both products an improvement in skin property, which appears softer and moisturised in 100% of cases and more homogeneous with 86% of agreement.

The volunteers recognised also for both products an effect on the colour of the stretchmarks and an attenuation of the skin roughness due to the stretchmarks. Moreover, two supplementary items are recognised for the product Skin Regenerator on the appearance and relief of the stretchmarks.

Concerning the cosmetic qualities, both products are well appreciated on their ease of application (100% of agreement), their time of penetration, and their non-sticky and non-greasy texture.

To conclude, in the experimental conditions of the study, a significant decrease in the visibility of the stretchmarks (in terms of colour and area) is observed on the whole panel after 56 days of application of the product skin regenerator SGep on the basis of colorimetric and morphologic analysis of the stretchmarks on photographs. Only a decrease in terms of surface is noted for the product SGspin.

However, no significant difference has been demonstrated between both products.

Moreover, the results of self-evaluation questionnaire show an improvement of the skin softness, the stretchmark colour and the skin roughness.

While illustrative and presently preferred embodiment(s) of the invention have been described in detail hereinabove, it is to be understood that the inventive concepts may be otherwise variously embodied and employed and that the appended claims are intended to be construed to include such variations except insofar as limited by the prior art.

The scope of the claims should not be limited by the preferred embodiments set forth in the examples, but should be given the broadest interpretation consistent with the description as a whole".

What is claimed is:

1. A Pickering formulation for use as an active ingredient in a pharmaceutical or cosmetic composition for regenerating skin cells, the Pickering formulation comprising:
    about 3% of organic-modified natural phyllosilicate;
    about 0.4% of xanthan gum;
    about 0.5% of sodium stearoyl glutamate;
    about 22% of Helianthus Annuus seed oil;
    about 0.5% of leuconostoc/radish root ferment filtrate;
    about 0.8% of glycerin & arginine HCl;
    about 0.5% of sodium benzoate; and
    about 0.2% of mixed tocopherol.

2. The Pickering formulation as claimed in claim 1, wherein the regeneration of the skin cells allows reducing the appearance of skin stretch marks on a human skin relative to the appearance of said skin stretch marks prior to the cosmetic use on the human skin.

3. The Pickering formulation as claimed in claim 1, wherein the regeneration of the skin cells allows healing skin cells after a burn.

4. The Pickering formulation as claimed in claim 3, wherein the burn is a sun burn.

5. The Pickering formulation as claimed in claim 1, wherein the pharmaceutical or cosmetic composition is free of sodium dodecyl sulfate, sodium lauryl sulfate, sodium olefin sulfonate, monoglycerides of fatty acids, diglycerides of fatty acids, polyethylene glycol esters of fatty acids or oils, propylene glycol esters of fatty acids or oils, glycereth esters of fatty acids or oils, and polyglycereth esters of fatty acids or oils.

6. The Pickering formulation as claimed in claim 1, wherein the Pickering formulation further comprises an emulsion of an oil phase and a water phase, the emulsion being stabilized with the organic-modified natural phyllosilicate.

7. The Pickering formulation as claimed in claim 1, wherein the organic-modified natural phyllosilicate is bentonite modified by a supplemental xanthan gum and citric acid.

8. The Pickering formulation as claimed in claim 6, wherein the oil phase is encapsulated into clay platelets.

9. The Pickering formulation as claimed in claim 6, wherein the organic-modified natural phyllosilicate comprises an organic compound selected from the group consisting of Xanthan gum, chitosan or citric acid.

10. The Pickering formulation as claimed in claim 6, wherein the emulsion is obtained by performing the following steps:
    i. adding an amount of the organic-modified natural phyllosilicate to the oil phase;
    ii. mixing the phyllosilicate and the oil phase to obtain a first mixture; and
    iii. adding the first mixture to a water phase while stirring;
wherein said steps i, ii and ii are performed at a temperature where the oil phase is liquid for a period of time of less than about 30 minutes.

11. The Pickering formulation as claimed in claim 10, wherein said steps i, ii and ii are performed at room temperature for a period of time of less than about 15 minutes.

12. The Pickering formulation as claimed in claim 6, wherein the organic-modified natural phyllosilicate comprises a phyllosilicate selected from the group consisting of vermiculites and smectites.

13. The Pickering formulation as claimed in claim 12, wherein the phyllosilicate is selected from the group consisting of sodium, potassium or calcium montmorillonites, bentonites, nonytronites, beidellites, volkonskoïtes, hectorites, saponites, sauconites, sobockites, stevensites, svinfordites and mixtures thereof.

14. The Pickering formulation as claimed in claim 12, wherein the phyllosilicate is hectorite, montmorillonite, bentonite or mixtures thereof.

15. A Pickering formulation for use as an active ingredient in a pharmaceutical or cosmetic composition for regenerating skin cells, the Pickering formulation comprising:
    about 2% of organic-modified natural phyllosilicate;
    about 0.4% of xanthan gum;
    about 0.5% of sodium stearoyl glutamate;
    about 22% of Helianthus Annuus seed oil;
    about 0.5% of leuconostoc/radish root ferment filtrate;
    about 0.8% of glycerin & arginine HCl;
    about 0.5% of sodium benzoate;
    about 0.2% of mixed tocopherol;
    about 1% bentonite, boroja patinoi extract & ulva lactuca extract; and
    about 72.1% water.

16. The Pickering formulation as claimed in claim 15, wherein the organic-modified natural phyllosilicate is bentonite modified by a supplemental xanthan gum and citric acid.

17. A sunscreen composition comprising a Pickering formulation, wherein the Pickering formulation provides a synergetic effect by boosting a sun protection factor, or SPF, of said sunscreen composition, the Pickering formulation comprising:
    about 3.3% organic-modified natural phyllosilicate;
    about 0.7% polyglyceryl-8 oleate;
    about 4% tricaprylin;
    about 4% balanites roxburghii seed oil;
    about 3% neopentyl glycol diheptanoate;
    about 28% caprylic/capric triglyceride, polyglyceryl-3 diisostearate, mica, titanium dioxide & zinc oxide;
    about 1% benzyl alcohol;
    about 0.05% mixed tocopherols;
    about 0.5% citric acid; and
    about 55.45% water.

18. The Pickering formulation as claimed in claim 17, wherein the organic-modified natural phyllosilicate is bentonite modified by a xanthan gum and citric acid.

19. The sunscreen composition of claim 17, wherein the composition is free of sodium dodecyl sulfate, sodium lauryl sulfate, sodium olefin sulfonate, monoglycerides of fatty acids, diglycerides of fatty acids, polyethylene glycol esters of fatty acids or oils, propylene glycol esters of fatty acids or oils, glycereth esters of fatty acids or oils, and polyglycereth esters of fatty acids or oils.

20. A method for treating skin cells of a human skin, the method comprising the step of:
    a. providing a Pickering formulation as defined in claim 1;
    b. applying the Pickering formulation to at least a portion of the skin in need of, such treatment; and c. letting the Pickering formulation on the skin for a given period of time.

21. The method of claim 20, wherein the Pickering formulation once applied on the skin forms a film or thin layer.

22. The method of claim 20, wherein the treatment allows reducing stretch marks of the human skin.

23. The method of claim 20, wherein the treatment allows healing skin cells damaged by a burn.

24. The method of claim 23, wherein the burn is a sun burn.

* * * * *